US011362123B2

(12) United States Patent
Ogita

(10) Patent No.: US 11,362,123 B2
(45) Date of Patent: Jun. 14, 2022

(54) IMAGING DEVICE, CAMERA MODULE, AND ELECTRONIC APPARATUS TO ENHANCE SENSITIVITY TO LIGHT

(71) Applicant: SONY SEMICONDUCTOR SOLUTIONS CORPORATION, Kanagawa (JP)

(72) Inventor: Tomoharu Ogita, Kanagawa (JP)

(73) Assignee: SONY SEMICONDUCTOR SOLUTIONS CORPORATION, Kanagawa (JP)

( * ) Notice: Subject to any disclaimer, the term of this patent is extended or adjusted under 35 U.S.C. 154(b) by 185 days.

(21) Appl. No.: 16/638,520

(22) PCT Filed: Aug. 8, 2018

(86) PCT No.: PCT/JP2018/029729
§ 371 (c)(1),
(2) Date: Feb. 12, 2020

(87) PCT Pub. No.: WO2019/039877
PCT Pub. Date: Feb. 28, 2019

(65) Prior Publication Data
US 2020/0365640 A1     Nov. 19, 2020

(30) Foreign Application Priority Data

Aug. 22, 2017 (JP) .............................. JP2017-159089

(51) Int. Cl.
| | |
|---|---|
| *H01L 27/146* | (2006.01) |
| *H04N 5/369* | (2011.01) |
| *G02B 7/04* | (2021.01) |

(52) U.S. Cl.
CPC .. *H01L 27/14632* (2013.01); *H01L 27/14618* (2013.01); *H01L 27/14621* (2013.01);
(Continued)

(58) Field of Classification Search
CPC ......... H01L 27/14632; H01L 27/14618; H01L 27/14621; H01L 27/14623;
(Continued)

(56) References Cited

U.S. PATENT DOCUMENTS

| | | | | |
|---|---|---|---|---|
| 2001/0055073 A1* | 12/2001 | Shinomiya | ........... | H04N 5/2254 |
| | | | | 348/374 |
| 2010/0103296 A1* | 4/2010 | Nakagiri | .............. | H04N 5/2257 |
| | | | | 348/294 |

(Continued)

FOREIGN PATENT DOCUMENTS

| | | |
|---|---|---|
| JP | 2006-041277 A | 2/2006 |
| JP | 2010-165939 A | 7/2010 |

(Continued)

OTHER PUBLICATIONS

International Search Report and Written Opinion of PCT Application No. PCT/JP2018/029729, dated Oct. 16, 2018, 09 pages of ISRWO.

*Primary Examiner* — Gevell V Selby
(74) *Attorney, Agent, or Firm* — Chip Law Group

(57) ABSTRACT

The present technology relates to an imaging device, a camera module, and an electronic apparatus that make it possible to reduce a profile of the camera module and to enhance sensitivity. The imaging device includes: a semiconductor substrate in which a light receiving section is formed that includes a plurality of pixels performing photoelectric conversion; and a reinforcing member that is disposed on side of the light receiving section of the semiconductor substrate and includes an opening in which a part opposed to the light receiving section is opened. The present technology is applicable to, for example, an imaging device that captures an image, a camera module that focuses light to capture an image, an electronic apparatus equipped with a camera function, a vehicle control system that is mounted (Continued)

on a vehicle, an endoscopic surgery system that is used in an endoscopic surgery, and the like.

7 Claims, 18 Drawing Sheets

(52) U.S. Cl.
CPC .. *H01L 27/14623* (2013.01); *H01L 27/14627* (2013.01); *H01L 27/14634* (2013.01); *H01L 27/14636* (2013.01); *H01L 27/14645* (2013.01); *H04N 5/369* (2013.01); *G02B 7/04* (2013.01)

(58) Field of Classification Search
CPC ......... H01L 27/14627; H01L 27/14634; H01L 27/14636; H01L 27/14645; H01L 27/14605; H01L 27/14625; H04N 5/369; H04N 5/2253; G02B 7/04; G02B 3/0056; G02B 5/201; G02B 13/0085; G02B 5/00; A61B 1/04

See application file for complete search history.

(56) References Cited

U.S. PATENT DOCUMENTS

| | | | |
|---|---|---|---|
| 2010/0321555 A1* | 12/2010 | Takeshita | H04N 5/2253 348/340 |
| 2011/0115002 A1* | 5/2011 | Tai | H01L 24/05 257/291 |
| 2018/0006070 A1 | 1/2018 | Isobe | |

FOREIGN PATENT DOCUMENTS

| | | |
|---|---|---|
| JP | 2015-135938 A | 7/2015 |
| WO | 2016/129409 A1 | 8/2016 |

* cited by examiner

[FIG. 1]
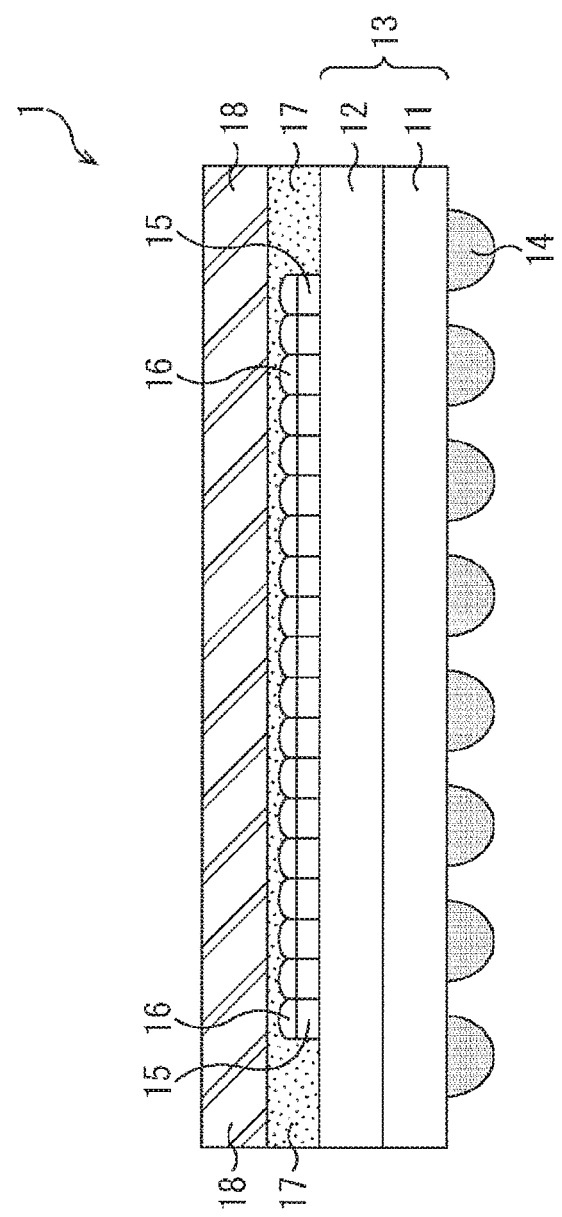

[FIG. 2A]
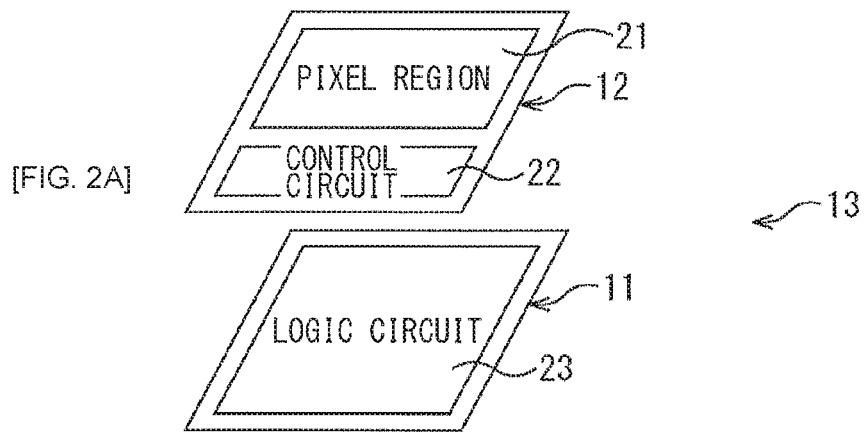
[FIG. 2B]
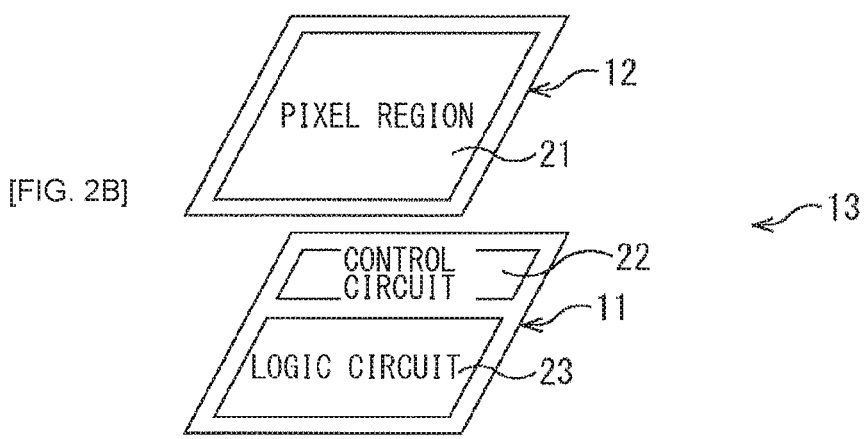

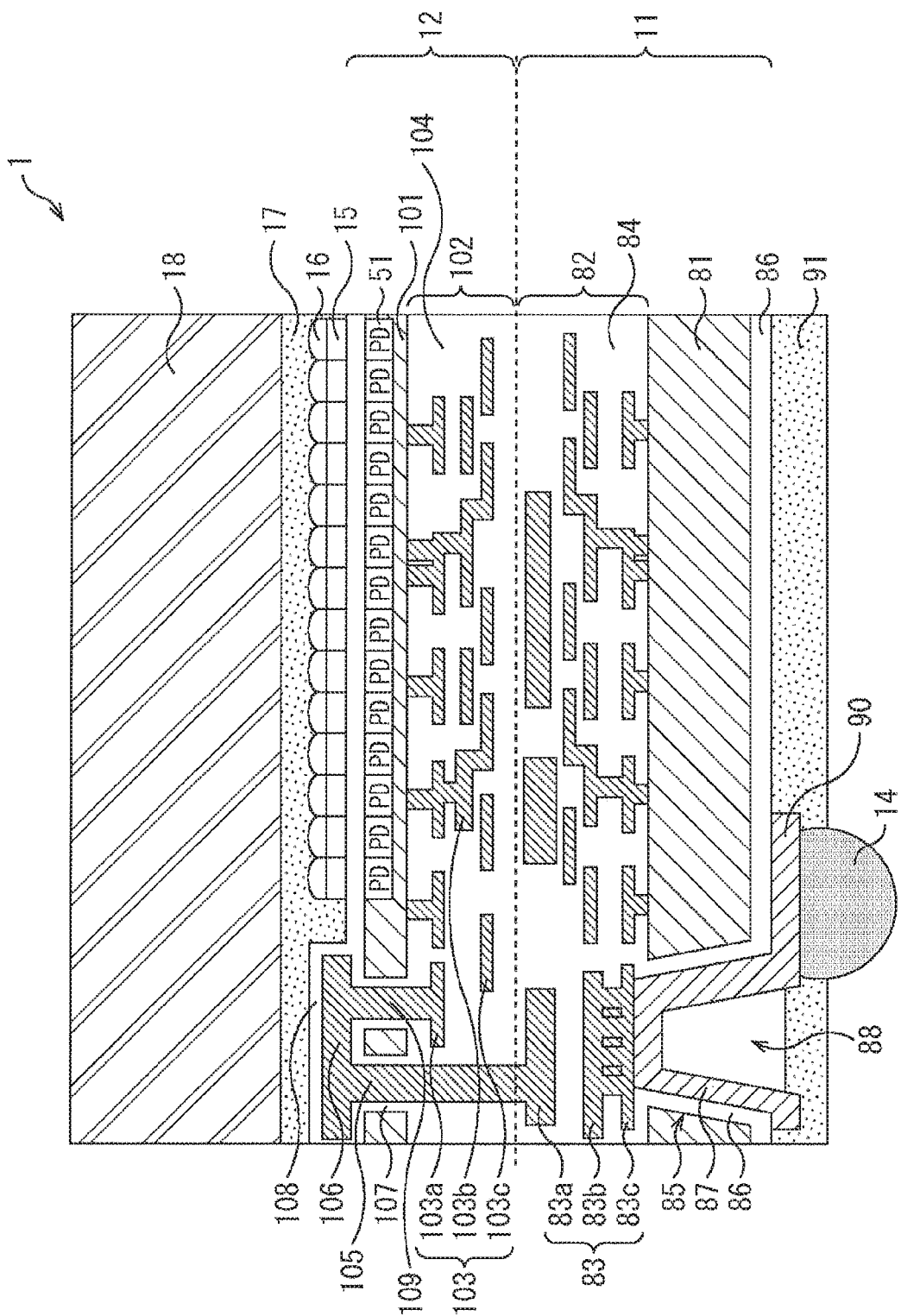
[FIG. 3]

[FIG. 4]
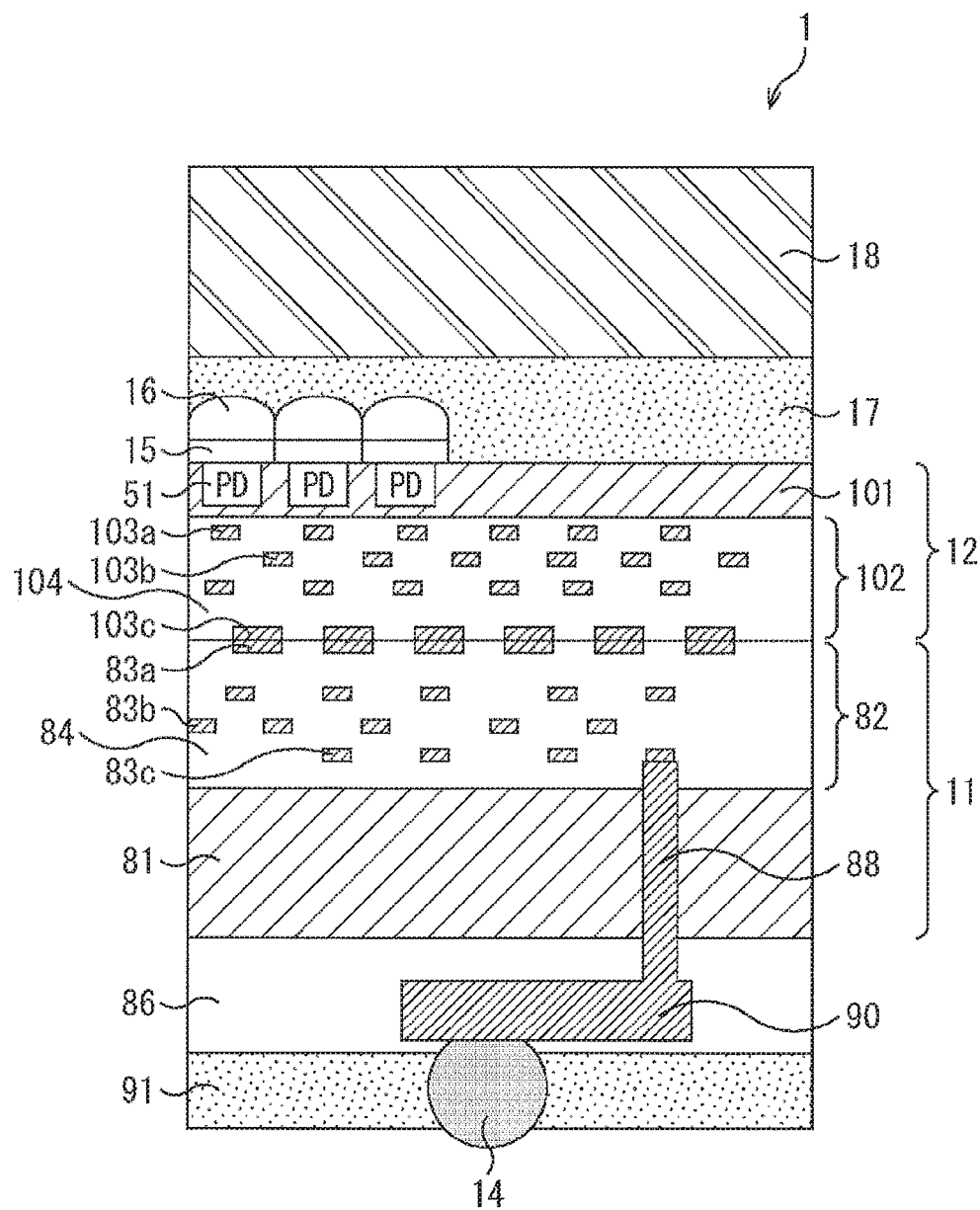

[FIG. 5]
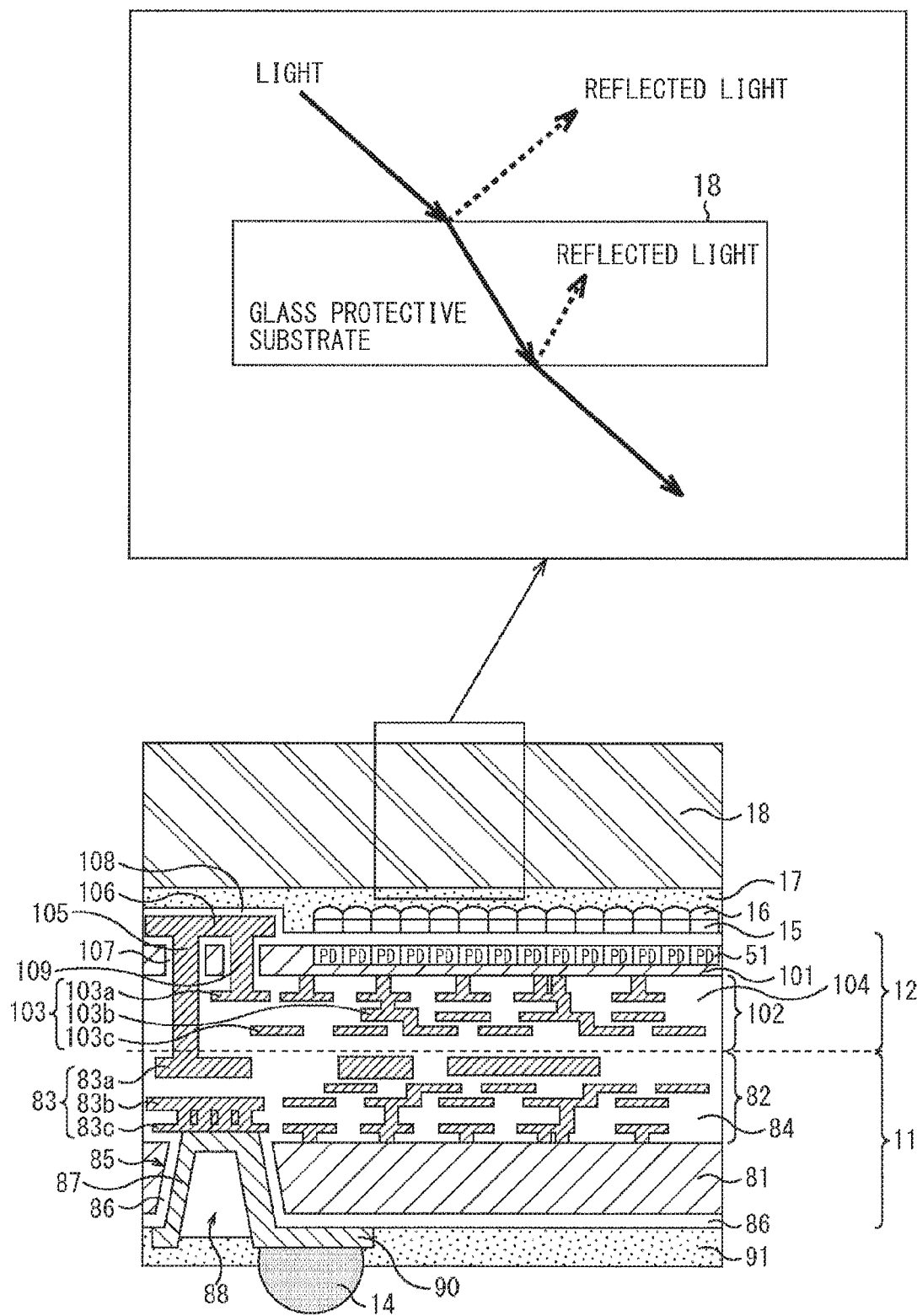

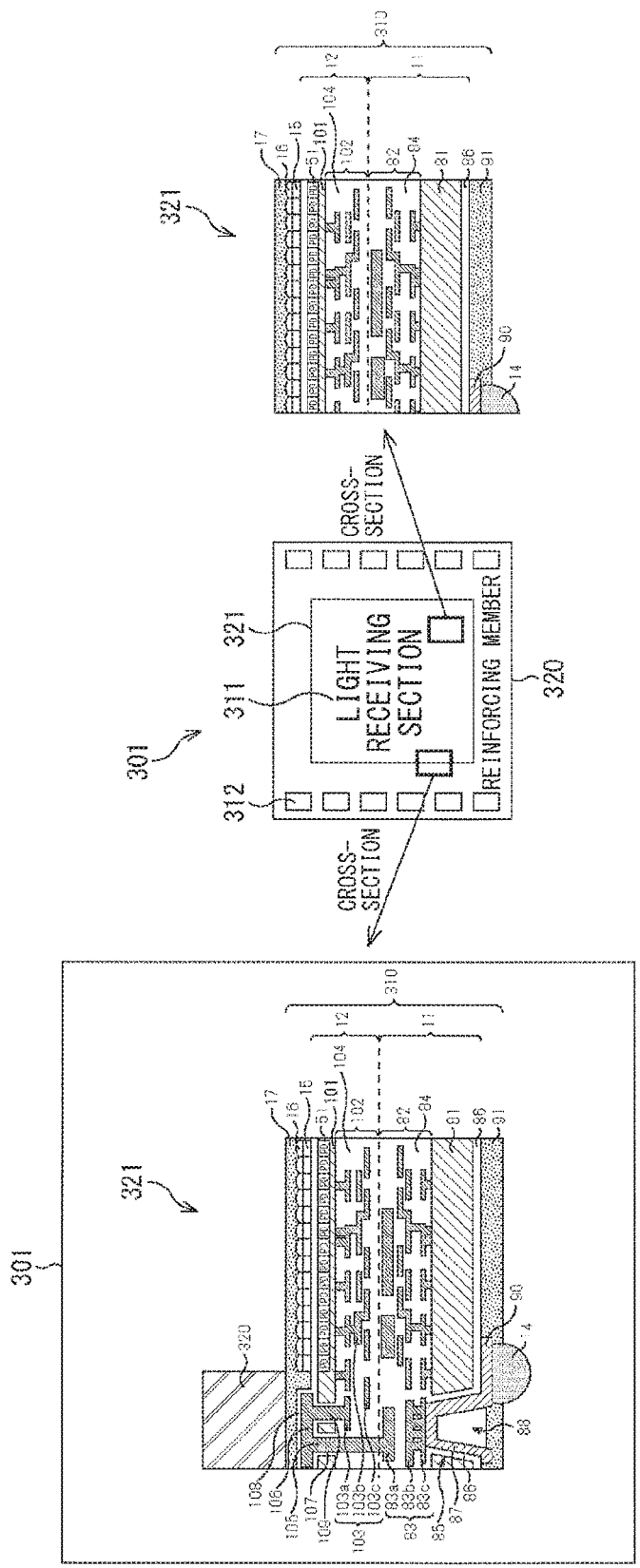
[FIG. 6]

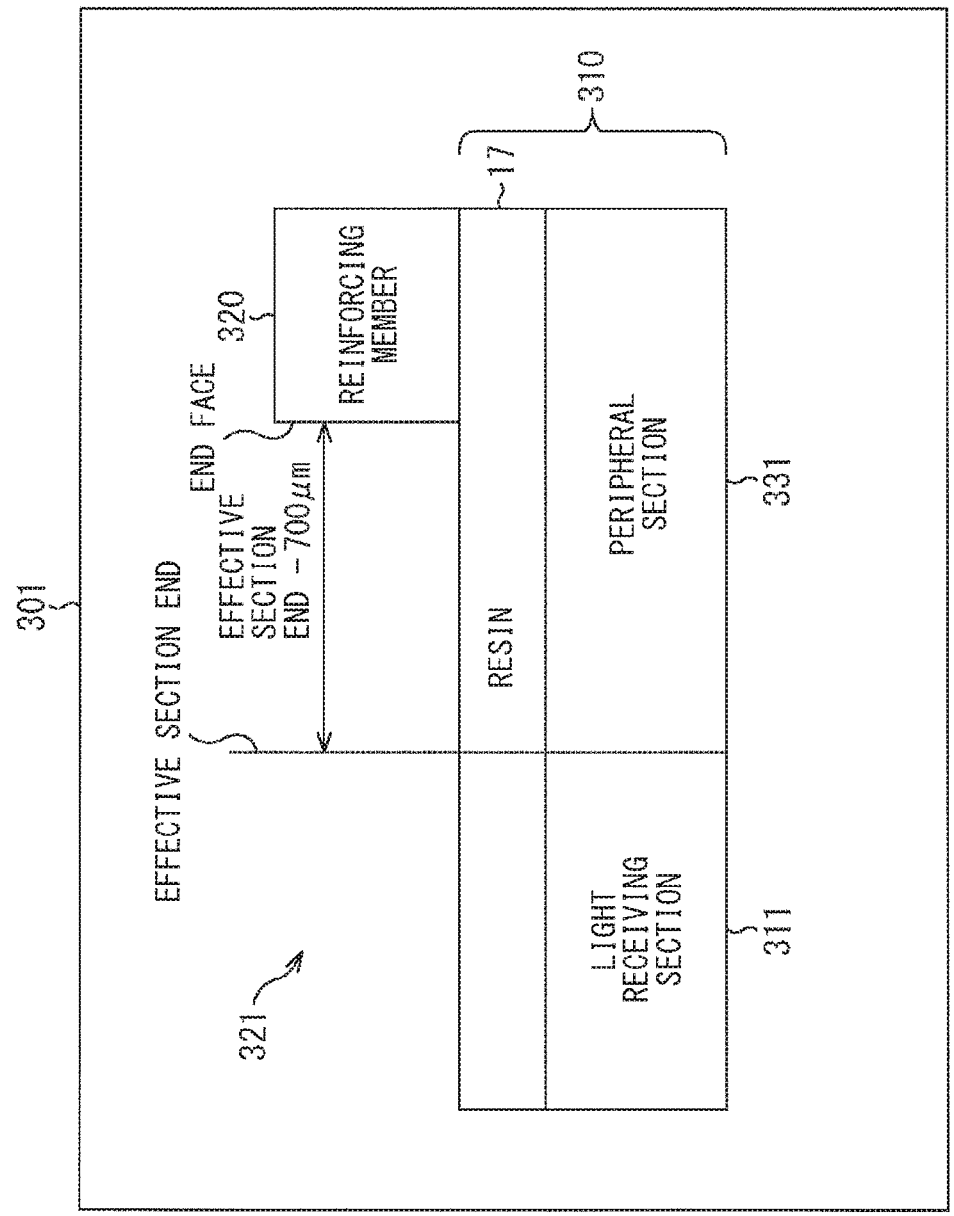

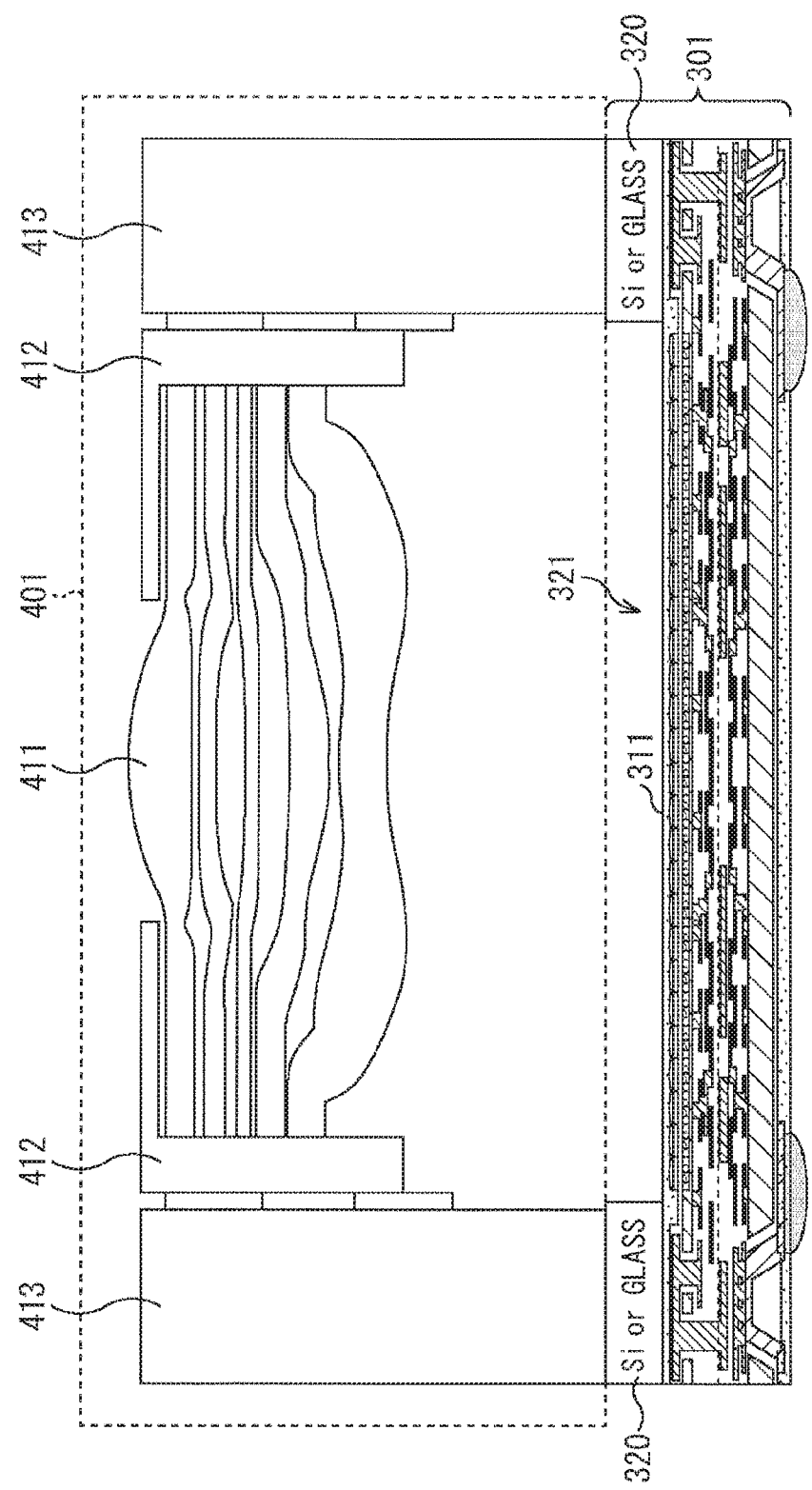
[FIG. 8]

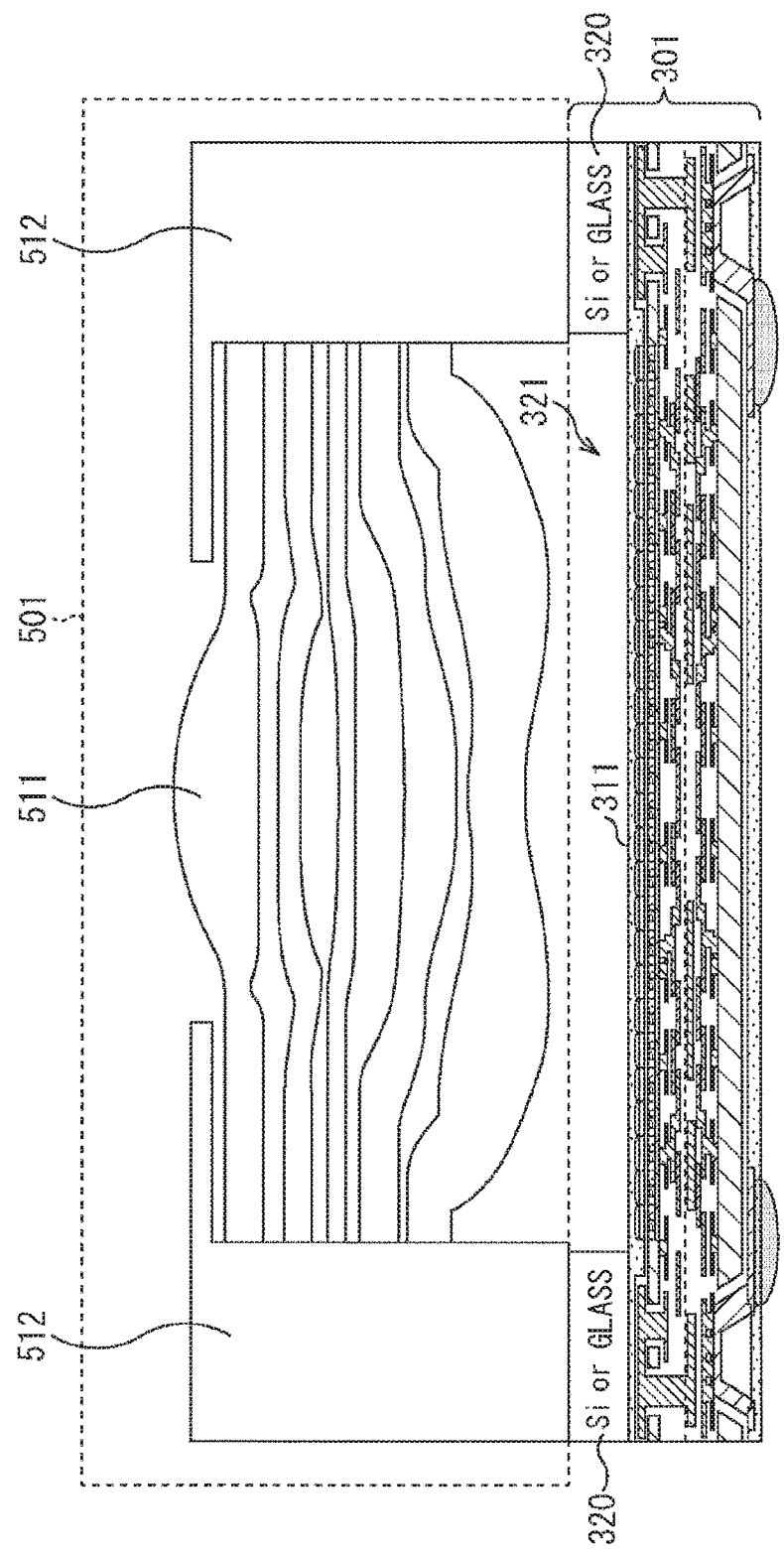
[FIG. 9]

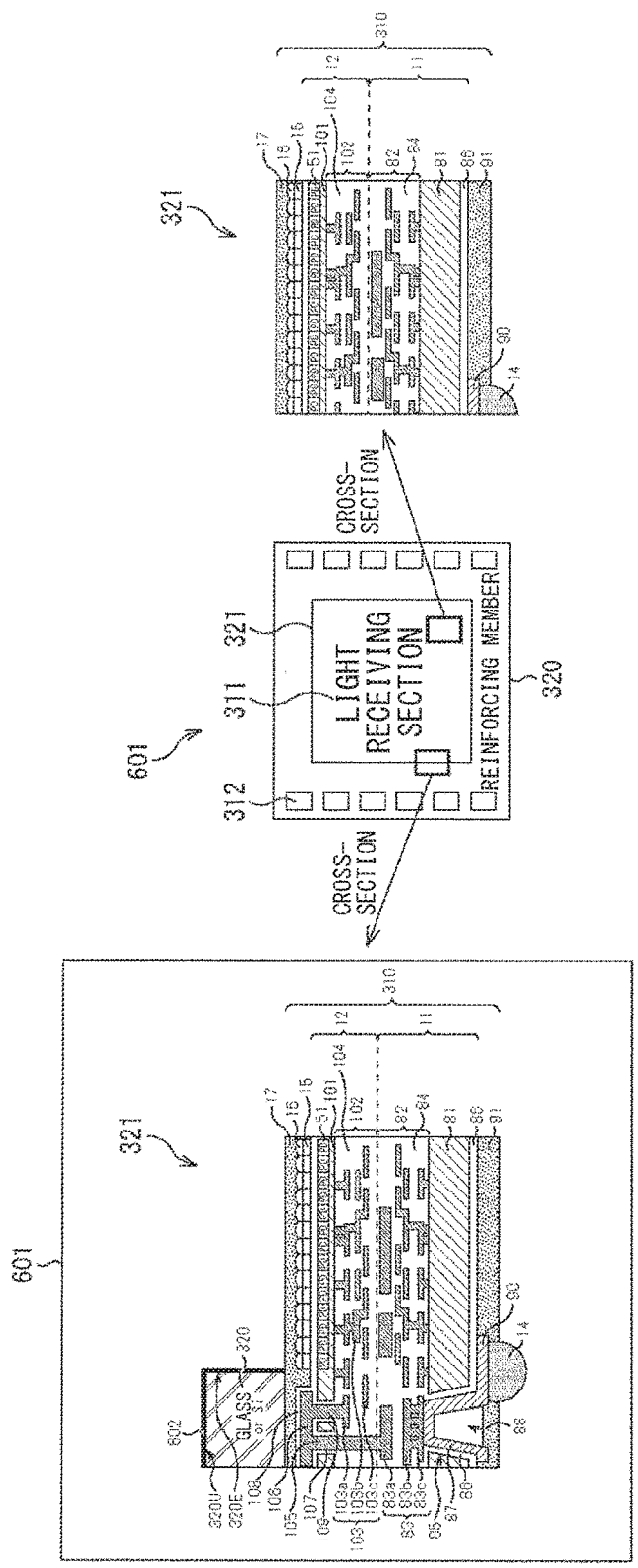
[FIG. 10]

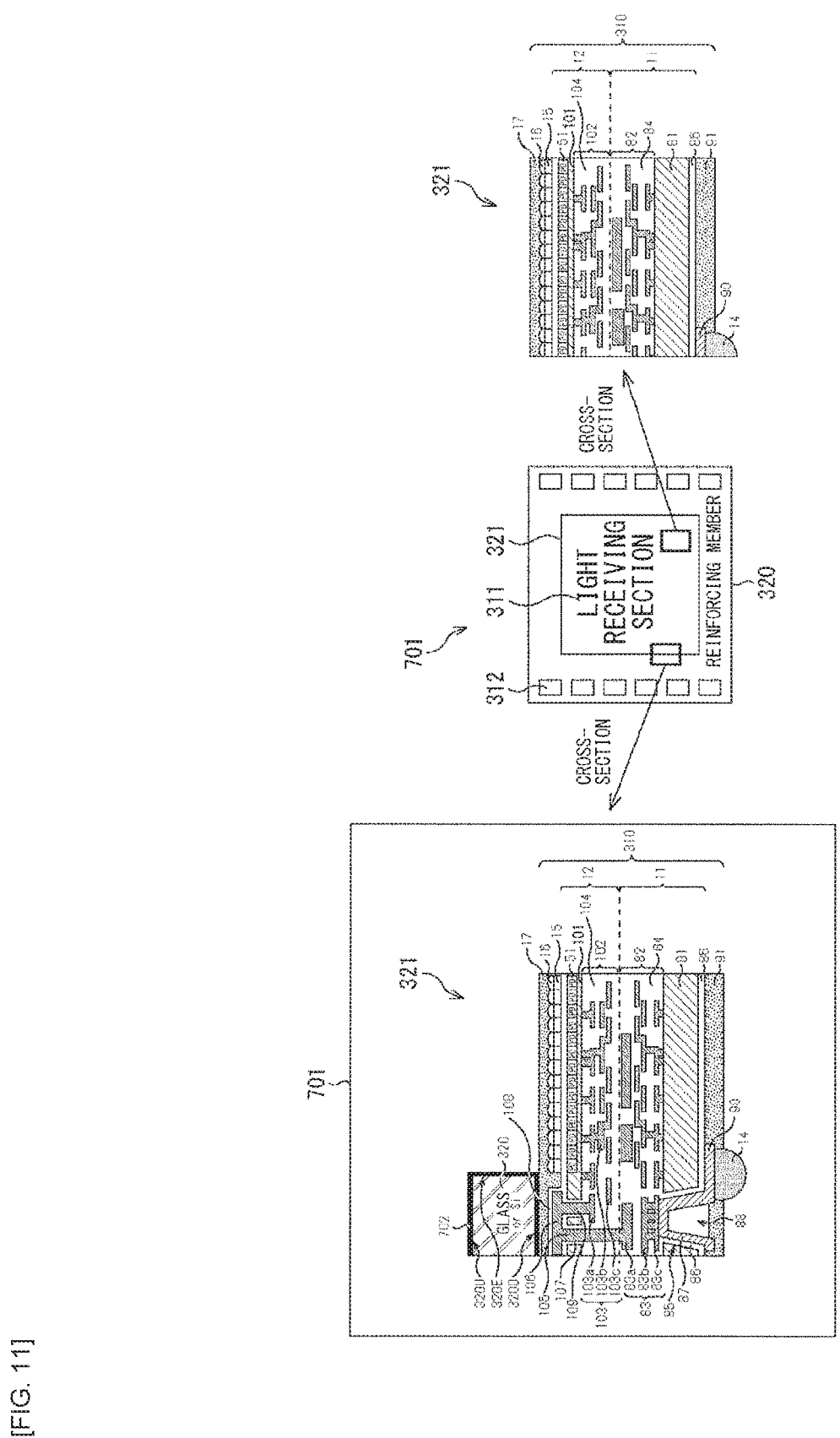
[FIG. 11]

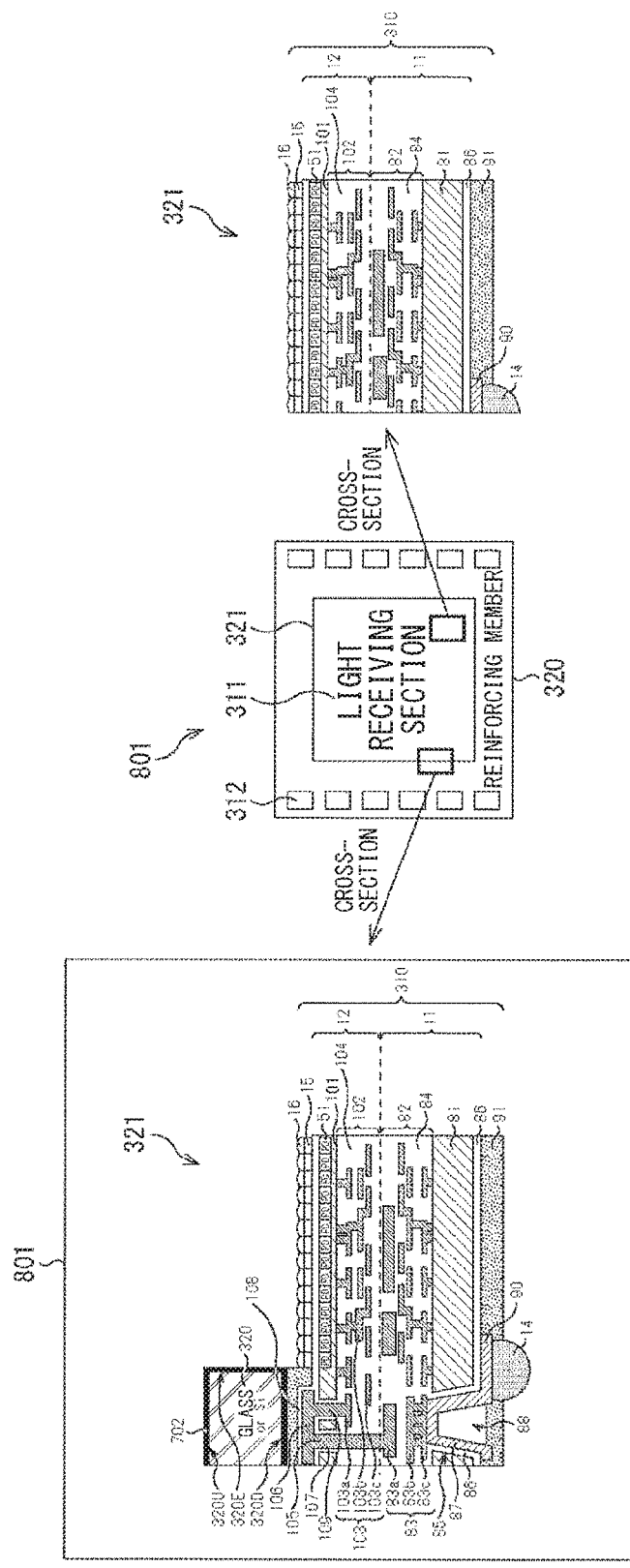
[FIG. 12]

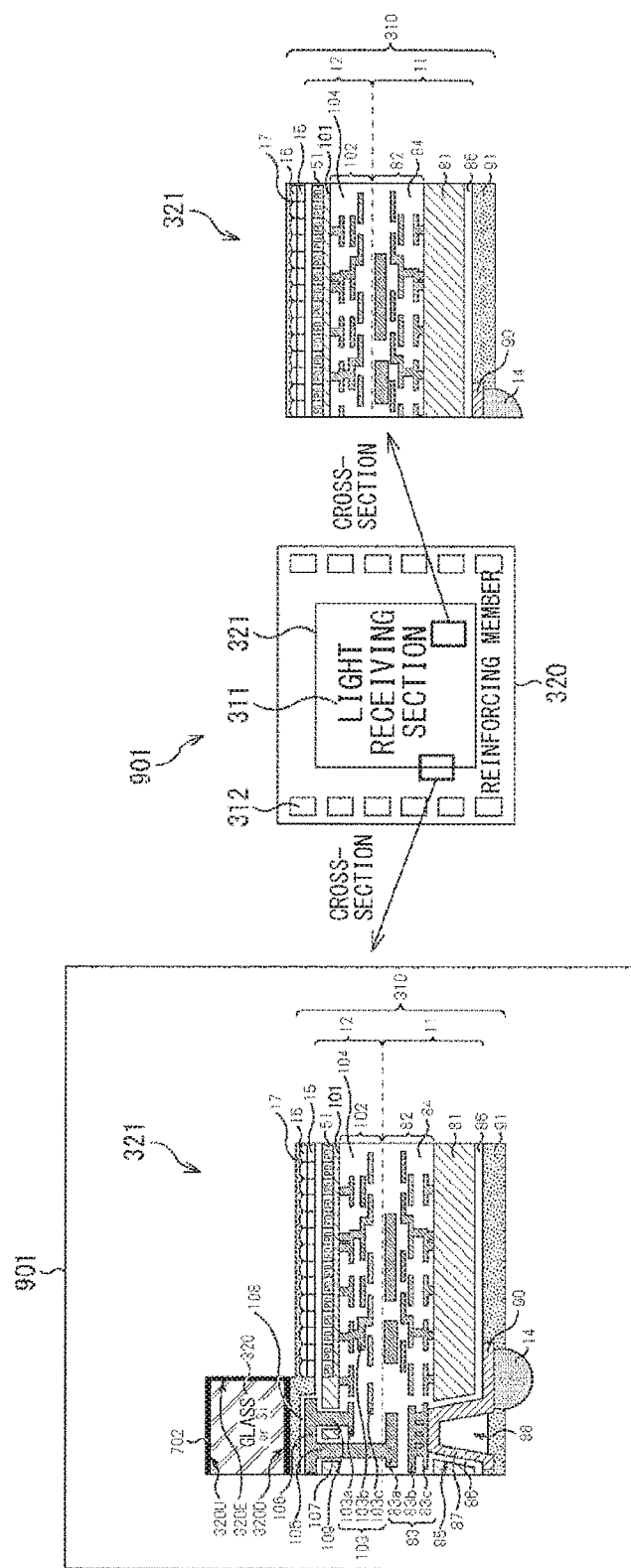
[FIG. 13]

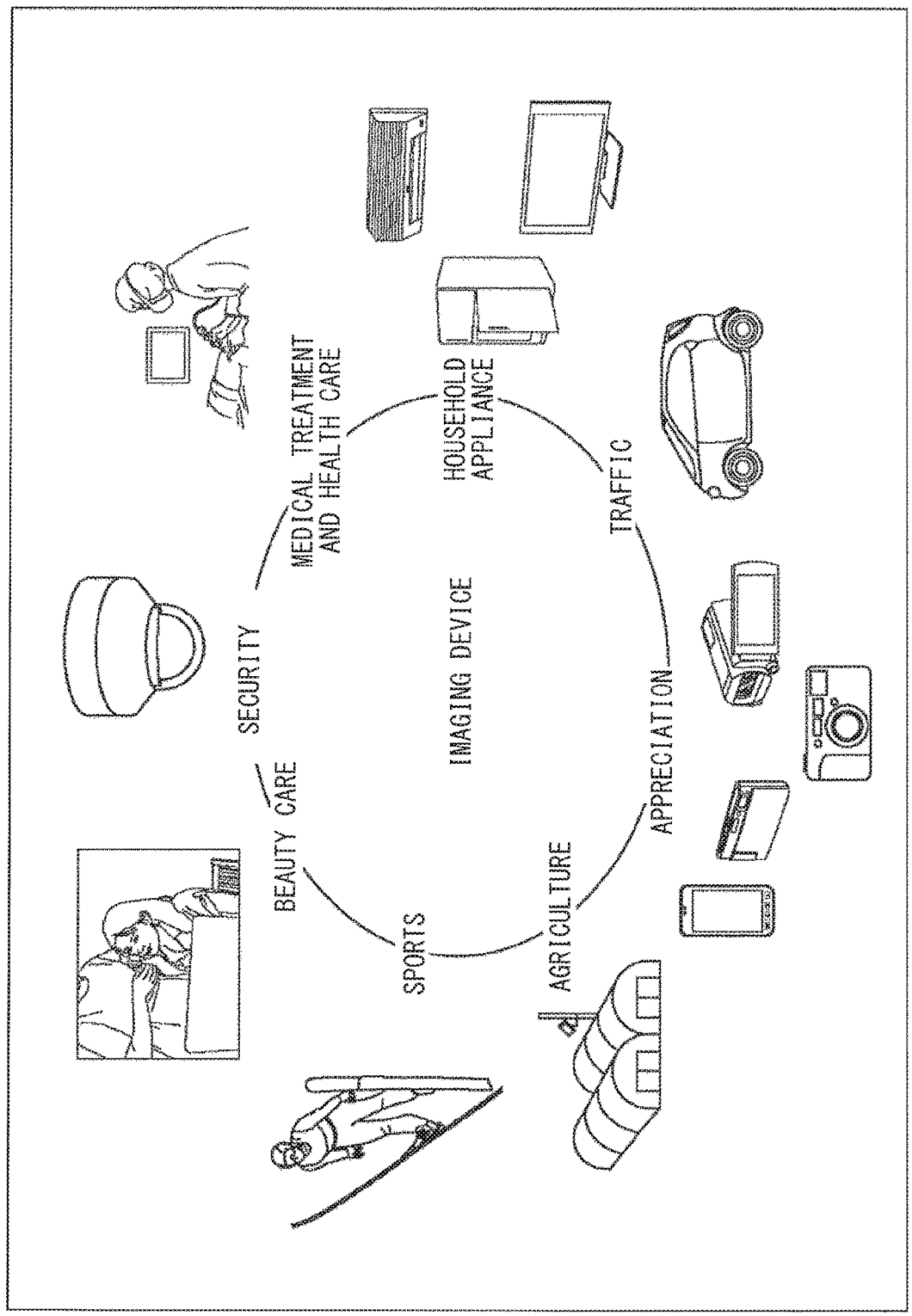
[FIG. 14]

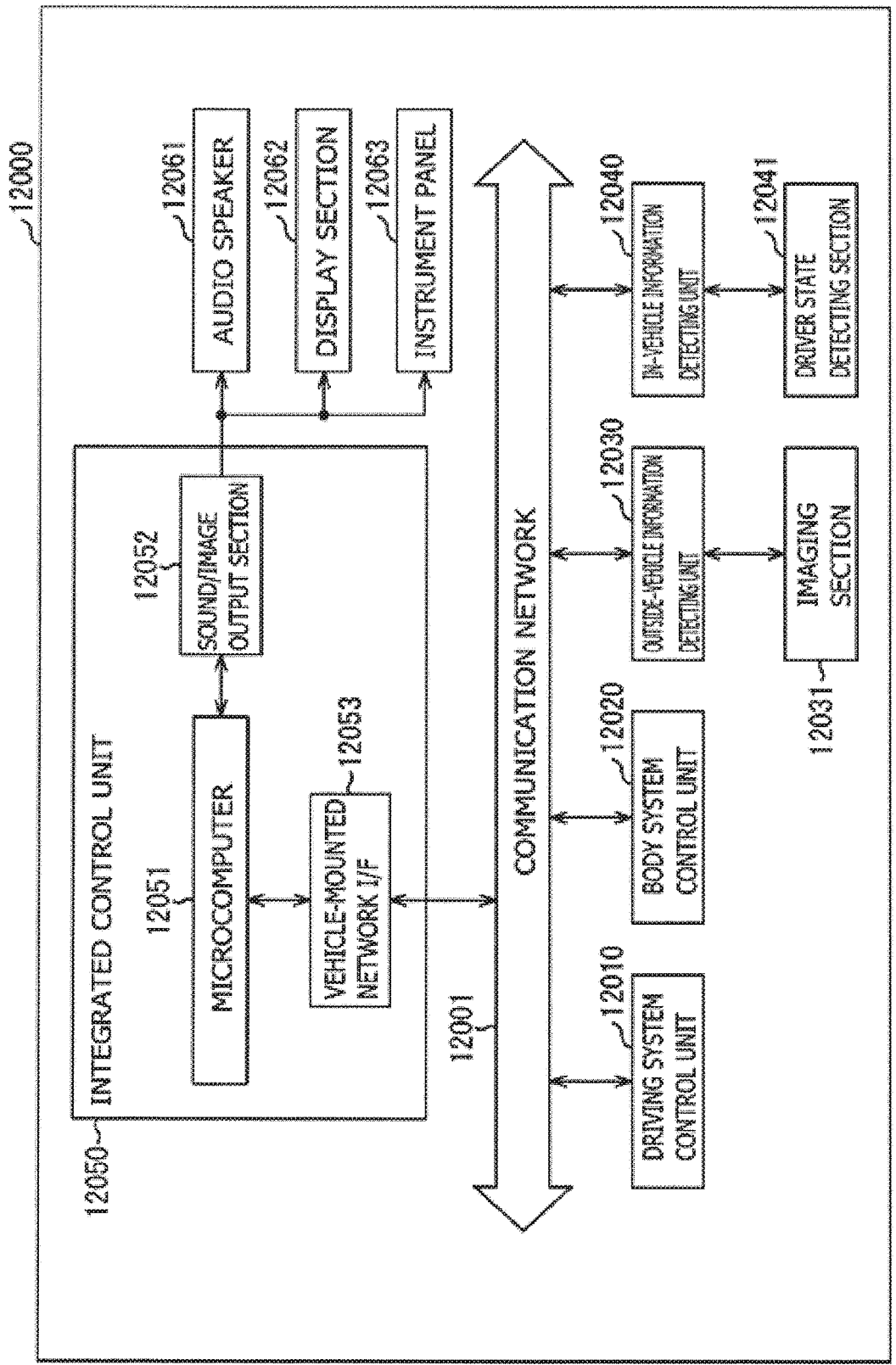
[FIG. 15]

[FIG. 16]
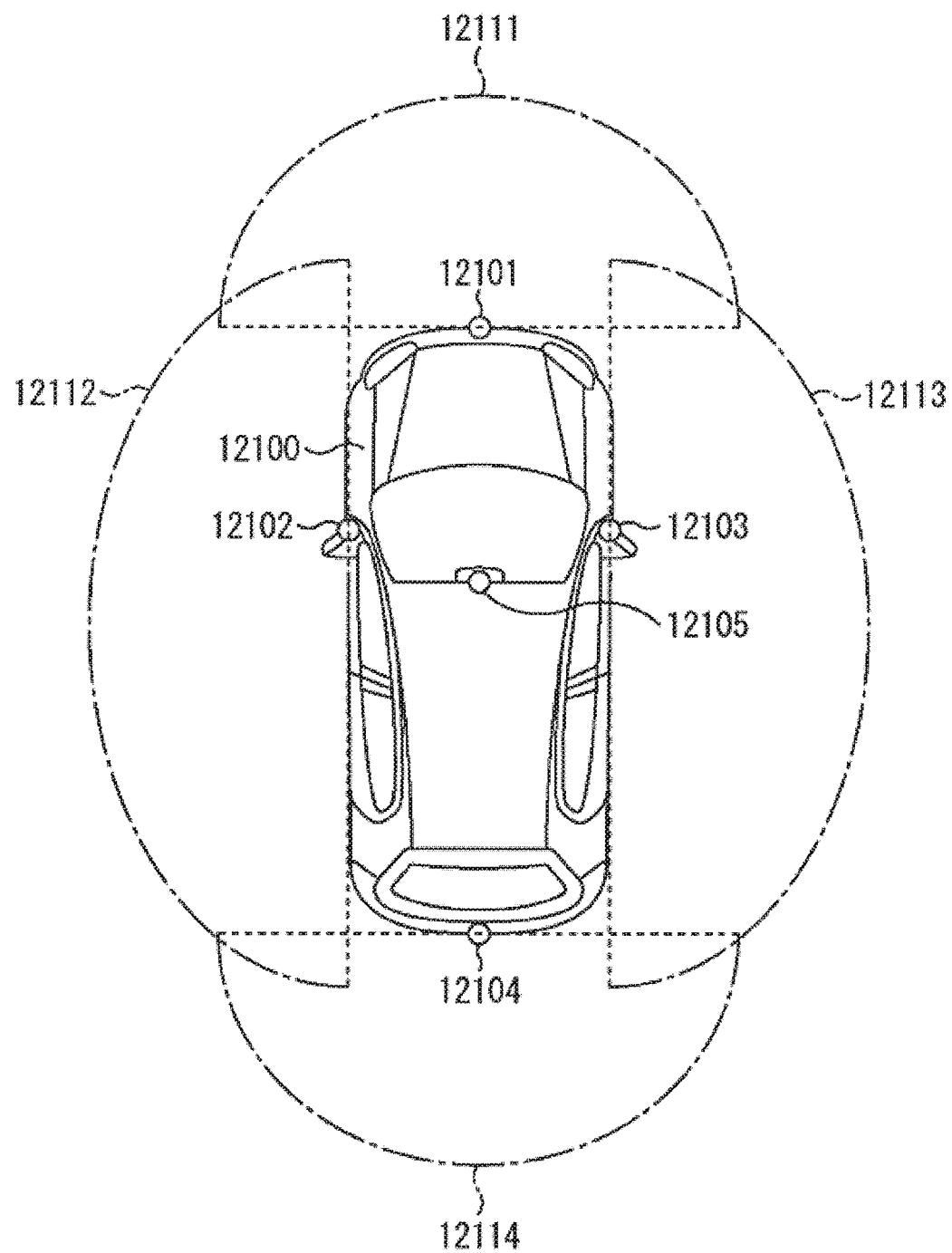

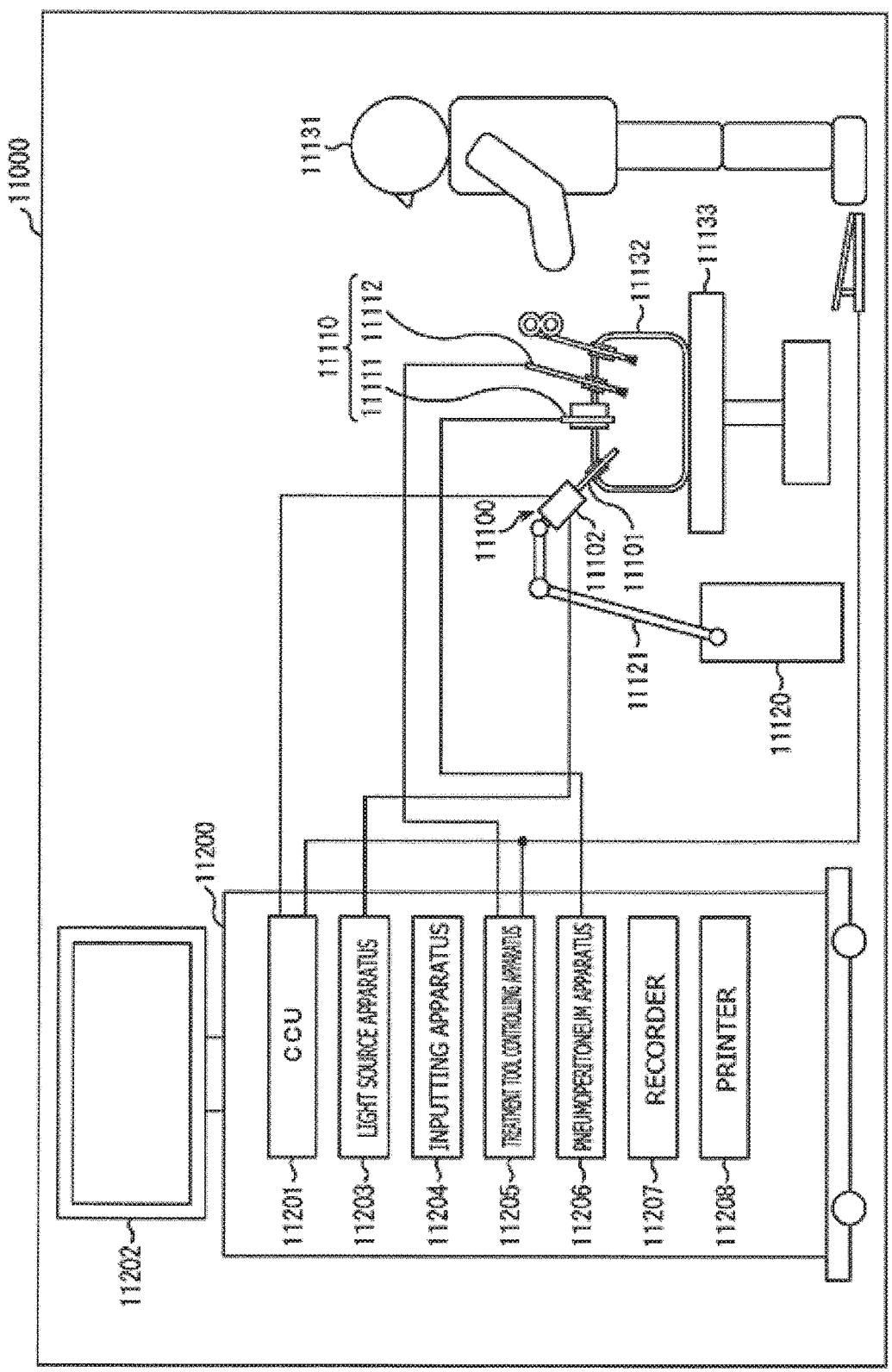
[FIG. 17]

[FIG. 18]
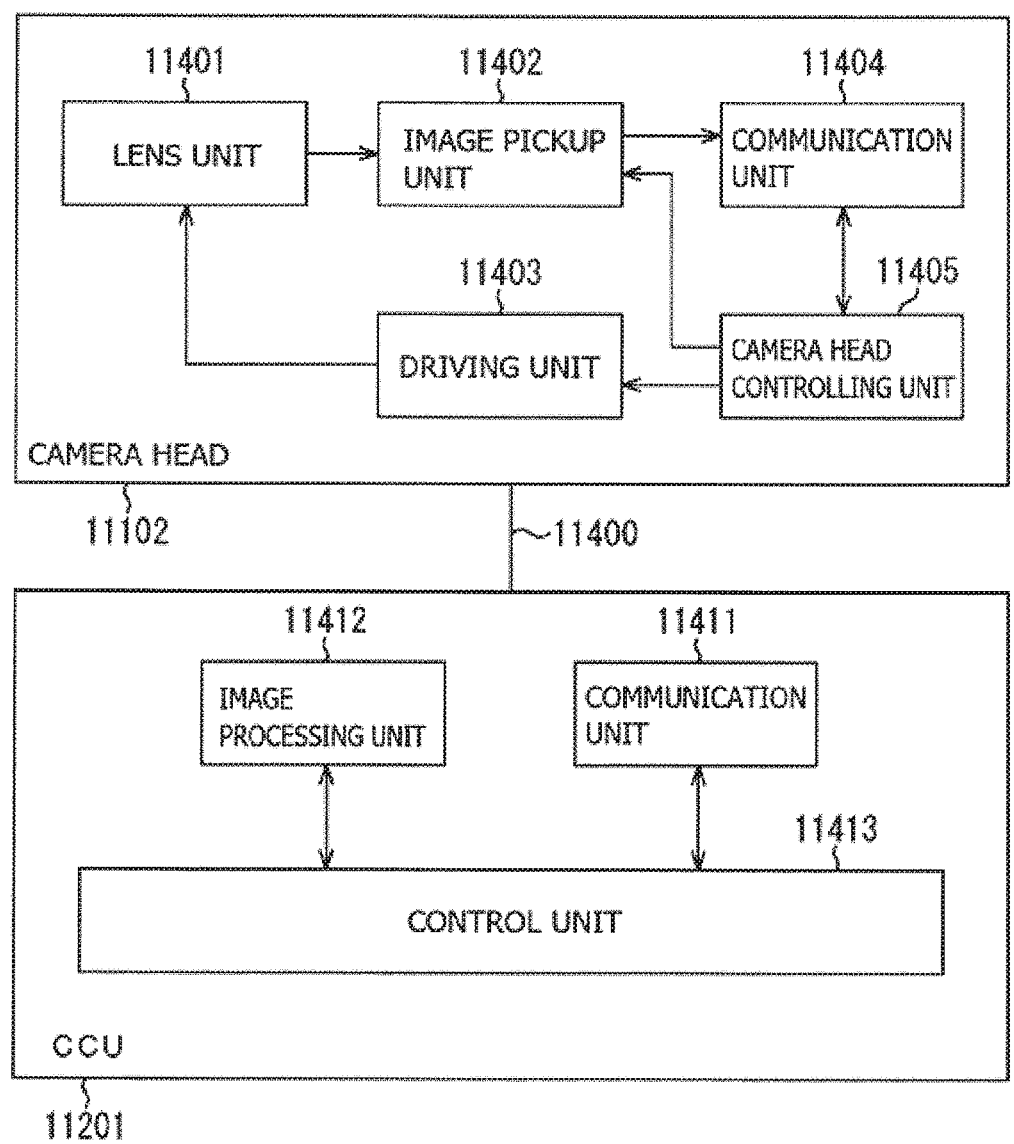

IMAGING DEVICE, CAMERA MODULE, AND ELECTRONIC APPARATUS TO ENHANCE SENSITIVITY TO LIGHT

CROSS REFERENCE TO RELATED APPLICATIONS

This application is a U.S. National Phase of International Patent Application No. PCT/JP2018/029729 filed on Aug. 8, 2018, which claims priority benefit of Japanese Patent Application No. JP 2017-159089 filed in the Japan Patent Office on Aug. 22, 2017. Each of the above-referenced applications is hereby incorporated herein by reference in its entirety.

TECHNICAL FIELD

The present technology relates to an imaging device, a camera module, and an electronic apparatus, and more particularly relates to, for example, an imaging device, a camera module, and an electronic apparatus that make it possible to reduce a profile of the camera module and to enhance sensitivity.

BACKGROUND ART

For example, PTL 1 discloses an imaging device that has a WLCSP (Wafer Level Chip Size Package) structure.

CITATION LIST

Patent Literature

PTL 1: Japanese Unexamined Patent Application Publication No. 2015-135938

SUMMARY OF THE INVENTION

Problems to be Solved by the Invention

On the uppermost part of an imaging device having a WLCSP structure, a glass protective substrate is provided, and in a camera module including such an imaging device and a lens module, light that enters the imaging device from the lens module passes through the glass protective substrate.

In the glass protective substrate, reflection and absorption of the light occur, and thus sensitivity of the imaging device to the light is lowered. In addition, the light passes through the glass protective substrate, and thus light refraction occurs, with the result that optical path length of the light is prolonged.

When the optical path length of the light is prolonged, a focal plane of the lens of the lens module is moved away from the lens. Consequently, it is necessary to increase a distance between the imaging device and the lens of the lens module, and thus the height of the camera module is increased.

The present technology has been made in view of circumstances as described above, and is intended to make it possible to reduce a profile of a camera module and to enhance sensitivity.

Means for Solving the Problems

An imaging device of the present technology is an imaging device having a WLCSP (Wafer Level Chip Size Package) structure including: a semiconductor substrate in which a light receiving section is formed that includes a plurality of pixels performing photoelectric conversion; and a reinforcing member that is disposed on side of the light receiving section of the semiconductor substrate and includes an opening in which a part opposed to the light receiving section is opened.

A camera module of the present technology is a camera module including: an optical system that focuses light; and an imaging device having a WLCSP (Wafer Level Chip Size Package) structure that receives the light to capture an image. The imaging device includes a semiconductor substrate in which a light receiving section is formed that includes a plurality of pixels performing photoelectric conversion, and a reinforcing member that is disposed on side of the light receiving section of the semiconductor substrate and includes an opening in which a part opposed to the light receiving section is opened.

An electronic apparatus of the present technology is an electronic apparatus including: an optical system that focuses light; and an imaging device having a WLCSP (Wafer Level Chip Size Package) structure that receives the light to capture an image. The imaging device includes a semiconductor substrate in which a light receiving section is formed that includes a plurality of pixels performing photoelectric conversion, and a reinforcing member that is disposed on side of the light receiving section of the semiconductor substrate and includes an opening in which a part opposed to the light receiving section is opened.

In the imaging device, the camera module, and the electronic apparatus of the present technology, a light receiving section including a plurality of pixels that performs photoelectric conversion is formed on a semiconductor substrate, and a reinforcing member is disposed on side of the light receiving section of the semiconductor substrate. The reinforcing member includes an opening in which a part opposed to the light receiving section is opened.

Effects of the Invention

According to the present technology, it is possible to reduce a profile of a camera module and to enhance sensitivity.

It is to be noted that effects described here are not necessarily limited and may be any of the effects described in the present disclosure.

BRIEF DESCRIPTION OF THE DRAWINGS

FIG. 1 is an external schematic view of a configuration example of an imaging device having a WLCSP (Wafer Level Chip Size Package) structure.

FIGS. 2A and 2B are perspective views of a schematic configuration example of a multilayer substrate.

FIG. 3 is a cross-sectional view of a configuration example of the imaging device.

FIG. 4 is a cross-sectional view of another configuration example of the imaging device.

FIG. 5 illustrates an optical path of light in the imaging device.

FIG. 6 includes a plan view and cross-sectional views of a configuration example of a first embodiment of an imaging device to which the present technology is applied.

FIG. 7 is a cross-sectional view of the imaging device for describing disposition of a reinforcing member with respect to a semiconductor substrate.

FIG. 8 is a cross-sectional view of a configuration example of a camera module using the imaging device.

FIG. 9 is a cross-sectional view of another configuration example of the camera module using the imaging device.

FIG. 10 includes a plan view and cross-sectional views of a configuration example of a second embodiment of the imaging device to which the present technology is applied.

FIG. 11 includes a plan view and cross-sectional views of a configuration example of a third embodiment of the imaging device to which the present technology is applied.

FIG. 12 includes a plan view and cross-sectional views of a configuration example of a fourth embodiment of the imaging device to which the present technology is applied.

FIG. 13 includes a plan view and cross-sectional views of a configuration example of a fifth embodiment of the imaging device to which the present technology is applied.

FIG. 14 illustrates usage examples where the imaging device is used.

FIG. 15 is a block diagram depicting an example of schematic configuration of a vehicle control system.

FIG. 16 is a diagram of assistance in explaining an example of installation positions of an outside-vehicle information detecting section and an imaging section.

FIG. 17 is a view depicting an example of a schematic configuration of an endoscopic surgery system.

FIG. 18 is a block diagram depicting an example of a functional configuration of a camera head and a camera control unit (CCU).

MODES FOR CARRYING OUT THE INVENTION

<1. Configuration Example of Imaging Device>

FIG. 1 is an external schematic view of a configuration example of an imaging device having a WLCSP (Wafer Level Chip Size Package) structure.

The imaging device 1 illustrated in FIG. 1 is a semiconductor package in which a multilayer substrate 13 configured by stacking a lower substrate 11 and an upper substrate 12 is packaged.

On the lower substrate 11, there is formed a plurality of solder balls 14 being backside electrodes for electrically coupling to an unillustrated external substrate.

On the upper surface of the upper substrate 12, a color filter 15 of R (red), G (green) or B (blue) and an on-chip lens 16 are formed. In addition, the upper substrate 12 is coupled, with a cavityless structure, to a glass protective substrate 18 for protecting the on-chip lens 16 with a glass seal resin 17 being interposed therebetween.

FIGS. 2A and 2B are perspective views of a schematic configuration example of the multilayer substrate 13.

For example, as illustrated in FIG. 2A, a pixel region 21 in which pixels that perform photoelectric conversion are two-dimensionally arranged and a control circuit 22 that performs control on the pixels are formed in the upper substrate 12, and a logic circuit 23 such as a signal processing circuit that processes pixel signals outputted from the pixels is formed in the lower substrate 11.

Alternatively, as illustrated in FIG. 2B, the multilayer substrate 13 may have a configuration in which only the pixel region 21 is formed in the upper substrate 12, and in which the control circuit 22 and the logic circuit 23 are formed in the lower substrate 11.

As described above, the logic circuit 23 or both the control circuit 22 and the logic circuit 23 are formed and stacked in the lower substrate 11 separate from the upper substrate 12 of the pixel region 21, thus making it possible to reduce size of the imaging device 1 as compared with a case where the pixel region 21, the control circuit 22, and the logic circuit 23 are disposed in a planar direction in one semiconductor substrate.

In the following description, the upper substrate 12 in which at least the pixel region 21 is formed is referred to as a pixel sensor substrate 12, and the lower substrate 11 in which at least the logic circuit 23 is formed is referred to as a logic substrate 11.

FIG. 3 is a cross-sectional view of a configuration example of the imaging device 1.

In the logic substrate 11, a multilayer wiring layer 82 is formed on upper side (side of the pixel sensor substrate 12) of a semiconductor substrate 81 (hereinafter referred to as a silicon substrate 81) configured by, for example, silicon (Si). The multilayer wiring layer 82 configures the control circuit 22 and the logic circuit 23 of FIGS. 2A and 2B.

The multilayer wiring layer 82 includes: a plurality of wiring layers 83 including a wiring layer 83a that is closest to the pixel sensor substrate 12 and is the uppermost layer, an intermediate wiring layer 83b, a wiring layer 83c that is closest to the silicon substrate 81 and is the lowermost layer, and the like; and an interlayer insulation film 84 formed between the wiring layers 83.

The plurality of wiring layers 83 is configured by, for example, copper (Cu), aluminum (Al), tungsten (W) and the like, and the interlayer insulation film 84 is formed by, for example, a silicon oxide film, a silicon nitride film or the like. In each of the wiring layers 83 and the interlayer insulation film 84, all the individual layers may be formed by the same material or two or more materials may be used for the individual layers.

In a predetermined position of the silicon substrate 81, a silicon through hole 85 is formed that penetrates the silicon substrate 81, and a coupling conductor 87 is embedded in an inner wall of the silicon through hole 85 with an insulation film 86 being interposed therebetween, thereby forming a silicon penetrating electrode (TSV: Through Silicon Via) 88. It is possible to use, for example, a SiO2 film, a SiN film, or the like to form the insulation film 86.

It is to be noted that, in the silicon penetrating electrode 88 illustrated in FIG. 3, the insulation film 86 and the coupling conductor 87 are formed as films along an inner wall surface, and thus the interior of the silicon through hole 85 is a cavity; however, the entire interior of the silicon through hole 85 may be embedded by the coupling conductor 87 depending on the inside diameter thereof. In other words, either the interior of the through hole may be embedded by the conductor or a portion thereof may be a cavity. The same is true for a chip penetrating electrode (TCV: Through Chip Via) 105 that is described later, and the like.

The coupling conductor 87 of the silicon penetrating electrode 88 is coupled to a rewiring line 90 that is formed on side of a lower surface of the silicon substrate 81, and the rewiring line 90 is coupled to the solder balls 14. It is possible to use, for example, copper (Cu), tungsten (W), titanium (Ti), tantalum (Ta), titanium tungsten alloy (TiW), polysilicon, and the like to form the coupling conductor 87 and the rewiring line 90.

A solder mask (solder resist) 91 is formed on the side of the lower surface of the silicon substrate 81 to cover the rewiring line 90 and the insulation film 86 except regions where the solder balls 14 are formed.

Meanwhile, in the pixel sensor substrate 12, a multilayer wiring layer 102 is formed on lower side (side of the logic substrate 11) of a semiconductor substrate 101 (hereinafter referred to as a silicon substrate 101) configured by silicon (Si). The multilayer wiring layer 102 configures the pixel circuit of the pixel region 21 in FIGS. 2A and 2B.

The multilayer wiring layer 102 includes: a plurality of wiring layers 103 including a wiring layer 103a that is closest to the silicon substrate 101 and is the uppermost layer, an intermediate wiring layer 103b, a wiring layer 103c that is closest to the logic substrate 11 and is the lowermost layer, and the like; and an interlayer insulation film 104 formed between the wiring layers 103.

It is possible to adopt, as materials used for the wiring layers 103 and the interlayer insulation film 104, the same types of materials as those of the wiring layers 83 and the interlayer insulation film 84 described above. In addition, the wiring layers 103 and the interlayer insulation film 104 are similar to the wiring layers 83 and the interlayer insulation film 84 described above also in that one or two or more materials may be used for the formation.

It is to be noted that, in the example of FIG. 3, the multilayer wiring layer 102 of the pixel sensor substrate 12 includes three wiring layers 103, and the multilayer wiring layer 82 of the logic substrate 11 includes four wiring layers 83; however, the total number of wiring layers is not limited thereto, and it is possible to form the multilayer wiring layer having any number of layers.

A plurality of photodiodes 51 formed by P-N junctions is formed inside the silicon substrate 101. The photodiodes 51 configure a pixel.

Although illustration is omitted, a plurality of pixel transistors such as transfer transistors, etc. that transfer charge of the photodiodes 51 are formed in the multilayer wiring layer 102 and the silicon substrate 101.

In predetermined positions of the silicon substrate 101 in which the color filter 15 and the on-chip lens 16 are not formed, a silicon penetrating electrode 109 that is coupled to the wiring layer 103a of the pixel sensor substrate 12 and a chip penetrating electrode 105 that is coupled to the wiring layer 83a of the logic substrate 11 are formed.

The chip penetrating electrode 105 and the silicon penetrating electrode 109 are coupled together with a coupling wiring line 106 formed on the upper surface of the silicon substrate 101. In addition, an insulation film 107 is formed between each of the silicon penetrating electrode 109 and the chip penetrating electrode 105 and the silicon substrate 101. Furthermore, on the upper surface of the silicon substrate 101, the color filter 15 and the on-chip lens 16 are formed with an insulation film (planarization film) 108 being interposed therebetween.

As described above, the multilayer substrate 13 of the imaging device 1 illustrated in FIG. 1 has a multilayer structure in which side of the multilayer wiring layer 82 of the logic substrate 11 and side of the multilayer wiring layer 102 of the pixel sensor substrate 12 are joined together. In FIG. 3, a surface on which the multilayer wiring layer 82 of the logic substrate 11 and the multilayer wiring layer 102 of the pixel sensor substrate 12 are joined together is indicated by a broken line.

In the multilayer substrate 13 of the imaging device 1, the wiring layers 103 of the pixel sensor substrate 12 and the wiring layers 83 of the logic substrate 11 are coupled by the two penetrating electrodes that are the silicon penetrating electrode 109 and the chip penetrating electrode 105, and the wiring layers 83 of the logic substrate 11 and the solder balls (back surface electrodes) 14 are coupled by the silicon penetrating electrode 88 and the rewiring line 90. In this way, it is possible to extremely minimize a plane area of the imaging device 1.

Furthermore, a cavityless structure is provided between the multilayer substrate 13 and the glass protective substrate 18 to join them together with the glass seal resin 17, and thus it is possible to reduce a dimension in a height direction (reduce the profile).

Hence, with the imaging device 1 illustrated in FIG. 1, it is possible to achieve a semiconductor package serving as an imaging device whose size is more reduced.

FIG. 4 is a cross-sectional view of another configuration example of the imaging device 1.

In FIG. 4, the logic substrate 11 and the pixel sensor substrate 12 are coupled together by metallic bonding between the wiring layers.

More specifically, the uppermost wiring layer 83a inside the multilayer wiring layer 82 of the logic substrate 11 and the lowermost wiring layer 103c inside the multilayer wiring layer 102 of the pixel sensor substrate 12 are coupled together by metallic bonding. As the materials of the wiring layer 83a and the wiring layer 103c, for example, copper (Cu) is suitable. It is to be noted that, in the example of FIG. 4, the wiring layer 83a and the wiring layer 103c are formed only on a junction surface of the logic substrate 11 and the pixel sensor substrate 12; however, metal (copper) serving as a junction wiring layer may be formed as a film on the entire junction surface.

In addition, in FIG. 4, illustration is simplified as compared with FIG. 3; the wiring layers 83 of the logic substrate 11 and the solder balls 14 are coupled by the silicon penetrating electrode 88 and the rewiring line 90 similarly to the case of FIG. 3.

FIG. 5 illustrates an optical path of light in the imaging device 1 of FIG. 3.

In the imaging device 1, light that enters the imaging device 1 from upper side in FIG. 5 through the glass protective substrate 18 is received by the pixel configured by the photodiodes 51, and thus an image is captured.

In the glass protective substrate 18, when the light enters the glass protective substrate 18, a portion of the light is reflected by the upper surface of the glass protective substrate 18. Furthermore, in the glass protective substrate 18, when the light exits from the glass protective substrate 18, a portion of the light is reflected by a lower surface of the glass protective substrate 18. In addition, in the glass protective substrate 18, a portion of the light that enters the glass protective substrate 18 is also absorbed. Hence, the light that is received in the pixel through the glass protective substrate 18 is lower in intensity than the light that is about to enter the glass protective substrate 18 (the light immediately before the entrance), with the result that sensitivity of the imaging device 1 to the light is lowered.

In addition, the light received by the pixel is refracted when passing through the glass protective substrate 18, and thus an optical path length is prolonged. In a case where a camera module includes the imaging device 1 and a lens module including a lens (optical system) that focuses light, when the optical path length is prolonged, a focal plane of the lens of the lens module is moved away from the lens, and thus it is necessary to increase a distance between the imaging device 1 and the lens of the lens module, with the result that the height (Total Height) of the camera module is increased.

As for the points described above, the same is true for the imaging device 1 of FIG. 4.

Hence, the present technology is intended to make it possible to reduce the profile of the camera module and to enhance the sensitivity.

The present technology is applicable to, for example, the imaging device having the WLCSP structure as illustrated in FIGS. 3 and 4. In the following, description is given of embodiments at the time when the present technology is applied to the imaging device having the WLCSP structure as illustrated in FIG. 3.

It is to be noted that the present technology is applicable to imaging devices having the WLCSP structure other than the imaging devices as illustrated in FIGS. 3 and 4. In addition, the present technology is also applicable to imaging devices that do not have the WLCSP structure.

<2. Configuration Example of First Embodiment of Imaging Device>

FIG. 6 includes a plan view and cross-sectional views of a configuration example of a first embodiment of the imaging device to which the present technology is applied.

It is to be noted that FIG. 6 illustrates a cross-sectional view of a part that includes an end surface of an opening 321 of a reinforcing member 320, and a cross-sectional view of a portion that does not include the end surface of the opening 321. The same is true also in the embodiments that is described later. In the diagram, parts corresponding to FIG. 3 are denoted with the same reference numerals, and the description thereof is omitted below as appropriate.

An imaging device 301 includes a semiconductor substrate 310 and the reinforcing member 320.

The semiconductor substrate 310 is configured similarly to the imaging device 1 of FIG. 3 except that the glass protective substrate 18 is not provided. That is, as illustrated in FIG. 1 that is the schematic view of the imaging device 1, the semiconductor substrate 310 includes the multilayer substrate 13 in which the lower substrate 11 and the upper substrate 12 are stacked, the solder balls 14, the color filter 15, the on-chip lens 16, and the glass seal resin 17.

In the plan view of FIG. 6, the semiconductor substrate 310 is substantially rectangular, and includes a light receiving section 311 and PADs 312.

The light receiving section 311 is disposed at a middle part of the semiconductor substrate 310, and corresponds to the pixel region 21 (FIGS. 2A and 2B) in which the pixels that perform photoelectric conversion are two-dimensionally arranged. The PADs 312 are disposed in a peripheral part of the semiconductor substrate 310, and are parts corresponding to, for example, the solder balls (FIG. 1) 14. Although, in the plan view of FIG. 6, the PADs 312 are illustrated to be seen through, the PADs 312 located below the semiconductor substrate 310 are actually invisible, hidden by the semiconductor substrate 310. The same is true also in the embodiments that is described later.

It is to be noted that the pixels included in the light receiving section 311 are so-called effective pixels through which pixel signals serving as the pixel values of an image to be captured by the imaging device 1 are obtained, and do not include OPB (Optical Black) pixels for detecting a black level. The OPB pixels are formed in a peripheral section of the semiconductor substrate 310 outside the light receiving section 311.

The reinforcing member 320 is a rectangular planar member in which size of its planar surface is substantially equal to that of the semiconductor substrate 310. The reinforcing member 320 is disposed on side of the light receiving section 311 serving as the upper side of the semiconductor substrate 310, and includes the opening 321 in which a part opposed to the light receiving section 311 is opened. It is possible to adopt, as the reinforcing member 320, for example, any member that has such a degree of strength as to make it possible to reinforce the semiconductor substrate 310, such as Si (silicon), glass, plastic or carbon.

The imaging device 301 differs from the imaging device 1 (FIGS. 1 and 3) in that the reinforcing member 320 is provided instead of the glass protective substrate 18.

The reinforcing member 320 includes the opening 321, and thus, in the imaging device 301, light enters the light receiving section 311 without intervention of the glass protective substrate 18. Hence, the light enters the light receiving section 311 without being refracted, and thus it is possible to prevent the optical path length of the light from being prolonged as in the imaging device 1.

Consequently, in a case where a camera module includes the imaging device 301 and the lens module including a lens that focuses light, it is not necessary to increase the distance between the light receiving section 311 and the lens of the lens module, unlike the imaging device 1, with the result that it is possible to reduce the profile of the camera module.

In addition, the imaging device 301 is not provided with the glass protective substrate 18, unlike the imaging device 1, on light incident side of the light receiving section 311, and thus there is substantially no reflection or absorption of the light occurring when the light passes through the glass protective substrate 18, thus making it possible to suppress the lowering in the sensitivity of the light caused by a decrease in the intensity of the light received by the light receiving section 311.

Next, description is given of a method of manufacturing the imaging device 301.

A manufacturing apparatus (unillustrated) that manufactures the imaging device 301 first configures the semiconductor substrate 310 in a state where the insulation film 86, the silicon penetrating electrode 88, and the solder mask 91 are not present. Further, the manufacturing apparatus further provides the reinforcing member 320 on the semiconductor substrate 310 in the state where the insulation film 86, the silicon penetrating electrode 88, and the solder mask 91 are not present, and forms the insulation film 86, the silicon penetrating electrode 88, and the solder mask 91 with the reinforcing member 320 being located at lower side, to complete the imaging device 301. The reinforcing member 320 reinforces the semiconductor substrate 310 when the insulation film 86, the silicon penetrating electrode 88, and the solder mask 91 are formed.

The reinforcing member 320 reinforces the semiconductor substrate 310 as described above, and thus it is preferable to adopt a member that has strength necessary for the reinforcement. As described above, it is possible to adopt, as the reinforcing member 320, for example, a member such as Si, glass, plastic, a carbon plate, or metal. Furthermore, it is possible to adopt, as the reinforcing member 320, a member that has a light shield structure (anti-reflection structure).

It is possible to achieve the light shield structure, for example, by adopting, as the reinforcing member 320, a member such as carbon having a light shield function with a black color or by providing a light shield film (plate) on the surface of the reinforcing member 320.

FIG. 7 is a cross-sectional view of the imaging device 301 for describing disposition of the reinforcing member 320 with respect to the semiconductor substrate 310.

A part outside the light receiving section 311 of the semiconductor substrate 310 is referred to as a peripheral section 331, and a boundary between the light receiving section 311 and the peripheral section 331 is referred to as an effective section end.

The reinforcing member 320 is configured such that the end surface of the opening 321 is positioned in a range extending about 700 μm from the effective section end toward the outside of the semiconductor substrate 310, and is disposed on the semiconductor substrate 310.

It is to be noted that the OPB pixels that are unillustrated are present in the peripheral section 331.

<3. Configuration Example of Camera Module>

FIG. 8 is a cross-sectional view of a configuration example of the camera module using the imaging device 301.

The camera module of FIG. 8 includes the imaging device 301 and a lens module 401.

The lens module 401 includes a lens 411, a lens barrel 412, and an actuator 413.

In the lens module 401, the lens 411 is fixed within the lens barrel 412, and the lens barrel 412 is supported by the actuator 413 provided outside the lens barrel 412.

The actuator 413 moves the lens barrel 412 in a direction of an optical axis of the lens 411 to thereby adjust a focus.

In FIG. 8, the actuator 413 of the lens module 401 configured as described above is adhered to the reinforcing member 320 to configure the camera module.

In the camera module configured as described above, light that has entered the lens 411 (optical system) is focused on the light receiving section 311. The light receiving section 311 receives the light from the lens 411, and performs photoelectric conversion to thereby capture an image.

FIG. 9 is a cross-sectional view of another configuration example of the camera module using the imaging device 301.

The camera module of FIG. 9 includes the imaging device 301 and a lens module 501.

The lens module 501 includes a lens 511 and a lens barrel 512.

It is to be noted that, it is possible to adopt, as the lens 511, for example, a WLL (Wafer Level Lens) and thus to form the entire camera module at a wafer level.

In the lens module 501, the lens 511 is fixed within the lens barrel 512. The lens module 501 differs from the lens module 401 illustrated in FIG. 8 in that the actuator 413 is not present.

In FIG. 9, the lens barrel 512 of the lens module 501 configured as described above is adhered to the reinforcing member 320 to configure the camera module.

In the camera module configured as described above, light that has entered the lens 511 is focused on the light receiving section 311. The light receiving section 311 receives the light from the lens 511, and performs photoelectric conversion to capture an image.

<4. Configuration Example of Second Embodiment of Imaging Device>

FIG. 10 includes a plan view and cross-sectional views of a configuration example of a second embodiment of the imaging device to which the present technology is applied.

It is to be noted that, in the diagram, parts corresponding to FIG. 6 are denoted with the same reference numerals, and the description thereof is omitted below as appropriate.

In FIG. 10, an imaging device 601 includes the semiconductor substrate 310 and the reinforcing member 320 configured by Si or glass. Hence, the imaging device 601 is configured similarly to the imaging device 301 of FIG. 6.

However, the imaging device 601 of FIG. 10 differs from the imaging device 301 in that a light shield structure (anti-reflection structure) 602 is provided in an upper surface 320U which is a surface, of the reinforcing member 320, on side opposite to the side opposed to the light receiving section 311 and in an end surface 320E of the reinforcing member 320 on side of the opening 321, while the imaging device 301 does not include the light shield structure 602.

In a case where the reinforcing member 320 includes the light shield structure 602 as described above, when the OPB pixels are present in the peripheral section 331 (FIG. 7) of the semiconductor substrate 310 below the reinforcing member 320, it is not necessary to provide a light shield film on the OPB pixels, with the result that it is possible to reduce the manufacturing cost of the imaging device 601 and to enhance the flexibility of the structure of the semiconductor substrate 310.

<5. Configuration Example of Third Embodiment of Imaging Device>

FIG. 11 includes a plan view and cross-sectional views of a configuration example of a third embodiment of the imaging device to which the present technology is applied.

It is to be noted that, in the diagram, parts corresponding to FIG. 10 are denoted with the same reference numerals, and the description thereof is omitted below as appropriate.

In FIG. 11, an imaging device 701 includes the semiconductor substrate 310 and the reinforcing member 320 configured by Si or glass. Hence, the imaging device 701 is configured similarly to the imaging device 601 of FIG. 10.

However, the imaging device 701 of FIG. 11 differs from the imaging device 601 which includes the light shield structure 602 only in the upper surface 320U and the end surface 320E in that a light shield structure (anti-reflection structure) 702 is provided not only in the upper surface 320U and the end surface 320E of the reinforcing member 320 but also in a lower surface 320D which is a surface on the side opposed to the light receiving section 311.

As described above, the imaging device 701 includes the light shield structure 702 not only in the upper surface 320U and the end surface 320E of the reinforcing member 320 but also in the lower surface 320D, thus suppressing the reflection of light that has entered the glass seal resin 17 below the reinforcing member 320 by the lower surface 320D, with the result that it is possible to suppress occurrence of flare and ghost caused by the reflection of the light by the lower surface 320D.

<6. Configuration Example of Fourth Embodiment of Imaging Device>

FIG. 12 includes a plan view and cross-sectional views of a configuration example of a fourth embodiment of the imaging device to which the present technology is applied.

It is to be noted that, in the diagram, parts corresponding to FIG. 11 are denoted with the same reference numerals, and the description thereof is omitted below as appropriate.

In FIG. 12, an imaging device 801 includes the semiconductor substrate 310 and the reinforcing member 320. Hence, the imaging device 801 is formed similarly to the imaging device 701 of FIG. 11.

However, the imaging device 801 of FIG. 12 differs from the imaging device 701 of FIG. 11 in which the glass seal resin 17 is provided in the opening 321 of the reinforcing member 320 and the part other than the opening 321 in that the glass seal resin 17 is not provided in (the upper part of) the light receiving section 311, i.e., in the opening 321 of the reinforcing member 320 and that the glass seal resin 17 is provided (only) in the part other than the opening 321 of the reinforcing member 320.

As described above, in the imaging device 801, the glass seal resin 17 is not provided in the light receiving section 311 (the opening 321), thus making light that enters the light receiving section 311 less likely to be reflected or absorbed by the glass seal resin 17. Consequently, it is possible to enhance the sensitivity of the light receiving section 311 to the light.

<7. Configuration Example of Fifth Embodiment of Imaging Device>

FIG. 13 includes a plan view and cross-sectional views of a configuration example of a fifth embodiment of the imaging device to which the present technology is applied.

It is to be noted that, in the diagram, parts corresponding to FIG. 11 are denoted with the same reference numerals, and the description thereof is omitted below as appropriate.

In FIG. 13, an imaging device 901 includes the semiconductor substrate 310 and the reinforcing member 320. Hence, the imaging device 901 is configured similarly to the imaging device 701 of FIG. 11.

However, the imaging device 901 of FIG. 13 differs from the imaging device 701 of FIG. 11 in which the glass seal resin 17 having a uniform thickness is provided in the opening 321 and the part other than the opening 321 in that the glass seal resin 17 in (the upper part of) the light receiving section 311, i.e., in the opening 321 of the reinforcing member 320 is embedded below relative to the glass seal resin 17 in the part other than the opening 321 and that thus the thickness of the glass seal resin 17 in the opening 321 is thinner than the thickness of the glass seal resin 17 in the part other than the opening 321.

As described above, in the imaging device 901, the thickness of the glass seal resin 17 in the opening 321 is thinner than the thickness of the glass seal resin 17 in the part other than the opening 321, thus making it possible to suppress the lowering in the sensitivity of the light receiving section 311 to the light caused by the reflection or the absorption of the light that enters the light receiving section 311 by the glass seal resin 17, as compared with the case of FIG. 11.

It is to be noted that the configuration of the glass seal resin 17 in the imaging device 801 of FIG. 12 and the configuration of the glass seal resin 17 in the imaging device 901 of FIG. 13 are also applicable to the imaging device 301 of FIG. 6 and to the imaging device 601 of FIG. 10.

In addition, it is possible to configure the camera module of FIG. 8 or FIG. 9 by any one of the imaging device 601 of FIG. 10 to the imaging device 901 of FIG. 13 other than the imaging device 301 of FIG. 6.

<8. Usage Examples of Imaging Device>

FIG. 14 illustrates usage examples where the imaging device 301 of FIG. 6 is used.

The imaging device 301 may be used in various electronic apparatuses that sense light such as visible light, infrared light, ultraviolet light and X-ray, for example, as described below. The same is true also for the imaging device 601 of FIG. 10 to the imaging device 901 of FIG. 13.

An electronic apparatus that captures an image to be used for appreciation, such as a digital camera and a mobile phone equipped with a camera function An electronic apparatus to be used for traffic for safety driving including an automatic stop and for recognition, etc. of the state of a driver, such as an vehicle-mounted sensor that captures images of a front, a rear, a surrounding, an inside, and the like of an automobile, a monitor camera that monitors traveling vehicles and a road, and a distance measuring sensor that measures a distance between vehicles, etc.

An electronic apparatus to be used for household appliances such as a TV, a refrigerator, and an air conditioner, in order to capture an image of a user's gesture and to perform an equipment operation in accordance with the gesture An electronic apparatus to be used for a medical treatment and a healthcare, such as an endoscope, an electron microscope, and an apparatus that captures an image of a blood vessel by means of light reception of infrared light An electronic apparatus to be used for security, such as a monitoring camera for an application of crime prevention and a camera for a person authentication application An electronic apparatus to be used for beauty care, such as a skin measuring instrument that captures an image of a skin and a microscope that captures an image of a scalp An electronic apparatus to be used for sports, such as an action camera and a wearable camera for a sports application, etc.

An electronic apparatus to be used for agriculture, such as a camera for monitoring states of fields and crops <9. Example of Application to Mobile Body>

A technique according to the present disclosure (the present technology) may be applied to various products. For example, the technique according to the present disclosure may be achieved as an apparatus to be mounted on a mobile body of any type, such as an automobile, an electric vehicle, a hybrid electric vehicle, a two-wheeled vehicle, a bicycle, a personal mobility, an aircraft, a drone, a vessel, and a robot.

FIG. 15 is a block diagram depicting an example of schematic configuration of a vehicle control system as an example of a mobile body control system to which the technology according to an embodiment of the present disclosure can be applied.

The vehicle control system 12000 includes a plurality of electronic control units connected to each other via a communication network 12001. In the example depicted in FIG. 15, the vehicle control system 12000 includes a driving system control unit 12010, a body system control unit 12020, an outside-vehicle information detecting unit 12030, an in-vehicle information detecting unit 12040, and an integrated control unit 12050. In addition, a microcomputer 12051, a sound/image output section 12052, and a vehicle-mounted network interface (I/F) 12053 are illustrated as a functional configuration of the integrated control unit 12050.

The driving system control unit 12010 controls the operation of devices related to the driving system of the vehicle in accordance with various kinds of programs. For example, the driving system control unit 12010 functions as a control device for a driving force generating device for generating the driving force of the vehicle, such as an internal combustion engine, a driving motor, or the like, a driving force transmitting mechanism for transmitting the driving force to wheels, a steering mechanism for adjusting the steering angle of the vehicle, a braking device for generating the braking force of the vehicle, and the like.

The body system control unit 12020 controls the operation of various kinds of devices provided to a vehicle body in accordance with various kinds of programs. For example, the body system control unit 12020 functions as a control device for a keyless entry system, a smart key system, a power window device, or various kinds of lamps such as a headlamp, a backup lamp, a brake lamp, a turn signal, a fog lamp, or the like. In this case, radio waves transmitted from a mobile device as an alternative to a key or signals of various kinds of switches can be input to the body system control unit 12020. The body system control unit 12020 receives these input radio waves or signals, and controls a door lock device, the power window device, the lamps, or the like of the vehicle.

The outside-vehicle information detecting unit 12030 detects information about the outside of the vehicle including the vehicle control system 12000. For example, the outside-vehicle information detecting unit 12030 is connected with an imaging section 12031. The outside-vehicle information detecting unit 12030 makes the imaging section 12031 image an image of the outside of the vehicle, and receives the imaged image. On the basis of the received image, the outside-vehicle information detecting unit 12030 may perform processing of detecting an object such as a human, a vehicle, an obstacle, a sign, a character on a road surface, or the like, or processing of detecting a distance thereto.

The imaging section 12031 is an optical sensor that receives light, and which outputs an electric signal corresponding to a received light amount of the light. The imaging section 12031 can output the electric signal as an image, or can output the electric signal as information about a measured distance. In addition, the light received by the imaging section 12031 may be visible light, or may be invisible light such as infrared rays or the like.

The in-vehicle information detecting unit 12040 detects information about the inside of the vehicle. The in-vehicle information detecting unit 12040 is, for example, connected with a driver state detecting section 12041 that detects the state of a driver. The driver state detecting section 12041, for example, includes a camera that images the driver. On the basis of detection information input from the driver state detecting section 12041, the in-vehicle information detecting unit 12040 may calculate a degree of fatigue of the driver or a degree of concentration of the driver, or may determine whether the driver is dozing.

The microcomputer 12051 can calculate a control target value for the driving force generating device, the steering mechanism, or the braking device on the basis of the information about the inside or outside of the vehicle which information is obtained by the outside-vehicle information detecting unit 12030 or the in-vehicle information detecting unit 12040, and output a control command to the driving system control unit 12010. For example, the microcomputer 12051 can perform cooperative control intended to implement functions of an advanced driver assistance system (ADAS) which functions include collision avoidance or shock mitigation for the vehicle, following driving based on a following distance, vehicle speed maintaining driving, a warning of collision of the vehicle, a warning of deviation of the vehicle from a lane, or the like.

In addition, the microcomputer 12051 can perform cooperative control intended for automatic driving, which makes the vehicle to travel autonomously without depending on the operation of the driver, or the like, by controlling the driving force generating device, the steering mechanism, the braking device, or the like on the basis of the information about the outside or inside of the vehicle which information is obtained by the outside-vehicle information detecting unit 12030 or the in-vehicle information detecting unit 12040.

In addition, the microcomputer 12051 can output a control command to the body system control unit 12020 on the basis of the information about the outside of the vehicle which information is obtained by the outside-vehicle information detecting unit 12030. For example, the microcomputer 12051 can perform cooperative control intended to prevent a glare by controlling the headlamp so as to change from a high beam to a low beam, for example, in accordance with the position of a preceding vehicle or an oncoming vehicle detected by the outside-vehicle information detecting unit 12030.

The sound/image output section 12052 transmits an output signal of at least one of a sound and an image to an output device capable of visually or auditorily notifying information to an occupant of the vehicle or the outside of the vehicle. In the example of FIG. 15, an audio speaker 12061, a display section 12062, and an instrument panel 12063 are illustrated as the output device. The display section 12062 may, for example, include at least one of an on-board display and a head-up display.

FIG. 16 is a diagram depicting an example of the installation position of the imaging section 12031.

In FIG. 16, the imaging section 12031 includes imaging sections 12101, 12102, 12103, 12104, and 12105.

The imaging sections 12101, 12102, 12103, 12104, and 12105 are, for example, disposed at positions on a front nose, sideview mirrors, a rear bumper, and a back door of the vehicle 12100 as well as a position on an upper portion of a windshield within the interior of the vehicle. The imaging section 12101 provided to the front nose and the imaging section 12105 provided to the upper portion of the windshield within the interior of the vehicle obtain mainly an image of the front of the vehicle 12100. The imaging sections 12102 and 12103 provided to the sideview mirrors obtain mainly an image of the sides of the vehicle 12100. The imaging section 12104 provided to the rear bumper or the back door obtains mainly an image of the rear of the vehicle 12100. The imaging section 12105 provided to the upper portion of the windshield within the interior of the vehicle is used mainly to detect a preceding vehicle, a pedestrian, an obstacle, a signal, a traffic sign, a lane, or the like.

Incidentally, FIG. 16 depicts an example of photographing ranges of the imaging sections 12101 to 12104. An imaging range 12111 represents the imaging range of the imaging section 12101 provided to the front nose. Imaging ranges 12112 and 12113 respectively represent the imaging ranges of the imaging sections 12102 and 12103 provided to the sideview mirrors. An imaging range 12114 represents the imaging range of the imaging section 12104 provided to the rear bumper or the back door. A bird's-eye image of the vehicle 12100 as viewed from above is obtained by superimposing image data imaged by the imaging sections 12101 to 12104, for example.

At least one of the imaging sections 12101 to 12104 may have a function of obtaining distance information. For example, at least one of the imaging sections 12101 to 12104 may be a stereo camera constituted of a plurality of imaging elements, or may be an imaging element having pixels for phase difference detection.

For example, the microcomputer 12051 can determine a distance to each three-dimensional object within the imaging ranges 12111 to 12114 and a temporal change in the distance (relative speed with respect to the vehicle 12100) on the basis of the distance information obtained from the imaging sections 12101 to 12104, and thereby extract, as a preceding vehicle, a nearest three-dimensional object in particular that is present on a traveling path of the vehicle 12100 and which travels in substantially the same direction as the vehicle 12100 at a predetermined speed (for example, equal to or more than 0 km/hour). Further, the microcomputer 12051 can set a following distance to be maintained in front of a preceding vehicle in advance, and perform automatic brake control (including following stop control), automatic acceleration control (including following start control), or the like. It is thus possible to perform cooperative control intended for automatic driving that makes the vehicle travel autonomously without depending on the operation of the driver or the like.

For example, the microcomputer 12051 can classify three-dimensional object data on three-dimensional objects into three-dimensional object data of a two-wheeled vehicle, a standard-sized vehicle, a large-sized vehicle, a pedestrian, a utility pole, and other three-dimensional objects on the basis of the distance information obtained from the imaging sections 12101 to 12104, extract the classified three-dimensional object data, and use the extracted three-dimensional object data for automatic avoidance of an obstacle. For example, the microcomputer 12051 identifies obstacles around the vehicle 12100 as obstacles that the driver of the vehicle 12100 can recognize visually and obstacles that are difficult for the driver of the vehicle 12100 to recognize visually. Then, the microcomputer 12051 determines a collision risk indicating a risk of collision with each obstacle. In a situation in which the collision risk is equal to or higher than a set value and there is thus a possibility of collision, the microcomputer 12051 outputs a warning to the driver via the audio speaker 12061 or the display section 12062, and performs forced deceleration or avoidance steering via the driving system control unit 12010. The microcomputer 12051 can thereby assist in driving to avoid collision.

At least one of the imaging sections 12101 to 12104 may be an infrared camera that detects infrared rays. The microcomputer 12051 can, for example, recognize a pedestrian by determining whether or not there is a pedestrian in imaged images of the imaging sections 12101 to 12104. Such recognition of a pedestrian is, for example, performed by a procedure of extracting characteristic points in the imaged images of the imaging sections 12101 to 12104 as infrared cameras and a procedure of determining whether or not it is the pedestrian by performing pattern matching processing on a series of characteristic points representing the contour of the object. When the microcomputer 12051 determines that there is a pedestrian in the imaged images of the imaging sections 12101 to 12104, and thus recognizes the pedestrian, the sound/image output section 12052 controls the display section 12062 so that a square contour line for emphasis is displayed so as to be superimposed on the recognized pedestrian. The sound/image output section 12052 may also control the display section 12062 so that an icon or the like representing the pedestrian is displayed at a desired position.

In the foregoing, the description has been given of one example of the vehicle control system to which the technique according to the present disclosure may be applied. The technique according to the present disclosure may be applied to the imaging section 12031, etc. of the configurations described above. Specifically, any one of the imaging device 301 of FIG. 6 and the imaging device 601 of FIG. 10 to the imaging device 901 of FIG. 13 is applicable to the imaging section 12031. Applying the technique according to the present disclosure to the imaging section 12031 makes it possible to reduce a profile of the imaging section 1203 land thus to reduce the size thereof as well as to enhance flexibility of installation of the imaging section 12031.

<10. Example of Application to Endoscopic Surgery System>

The technique according to the present disclosure (the present technology) is applicable to various products. For example, the technique according to the present disclosure may be applied to an endoscopic surgery system.

FIG. 17 is a view depicting an example of a schematic configuration of an endoscopic surgery system to which the technology according to an embodiment of the present disclosure (present technology) can be applied.

In FIG. 17, a state is illustrated in which a surgeon (medical doctor) 11131 is using an endoscopic surgery system 11000 to perform surgery for a patient 11132 on a patient bed 11133. As depicted, the endoscopic surgery system 11000 includes an endoscope 11100, other surgical tools 11110 such as a pneumoperitoneum tube 11111 and an energy device 11112, a supporting arm apparatus 11120 which supports the endoscope 11100 thereon, and a cart 11200 on which various apparatus for endoscopic surgery are mounted.

The endoscope 11100 includes a lens barrel 11101 having a region of a predetermined length from a distal end thereof to be inserted into a body cavity of the patient 11132, and a camera head 11102 connected to a proximal end of the lens barrel 11101. In the example depicted, the endoscope 11100 is depicted which includes as a rigid endoscope having the lens barrel 11101 of the hard type. However, the endoscope 11100 may otherwise be included as a flexible endoscope having the lens barrel 11101 of the flexible type.

The lens barrel 11101 has, at a distal end thereof, an opening in which an objective lens is fitted. A light source apparatus 11203 is connected to the endoscope 11100 such that light generated by the light source apparatus 11203 is introduced to a distal end of the lens barrel 11101 by a light guide extending in the inside of the lens barrel 11101 and is irradiated toward an observation target in a body cavity of the patient 11132 through the objective lens. It is to be noted that the endoscope 11100 may be a forward-viewing endoscope or may be an oblique-viewing endoscope or a side-viewing endoscope.

An optical system and an image pickup element are provided in the inside of the camera head 11102 such that reflected light (observation light) from the observation target is condensed on the image pickup element by the optical system. The observation light is photo-electrically converted by the image pickup element to generate an electric signal corresponding to the observation light, namely, an image signal corresponding to an observation image. The image signal is transmitted as RAW data to a CCU 11201.

The CCU 11201 includes a central processing unit (CPU), a graphics processing unit (GPU) or the like and integrally controls operation of the endoscope 11100 and a display apparatus 11202. Further, the CCU 11201 receives an image signal from the camera head 11102 and performs, for the image signal, various image processes for displaying an image based on the image signal such as, for example, a development process (demosaic process).

The display apparatus 11202 displays thereon an image based on an image signal, for which the image processes have been performed by the CCU 11201, under the control of the CCU 11201.

The light source apparatus 11203 includes a light source such as, for example, a light emitting diode (LED) and supplies irradiation light upon imaging of a surgical region to the endoscope 11100.

An inputting apparatus 11204 is an input interface for the endoscopic surgery system 11000. A user can perform inputting of various kinds of information or instruction inputting to the endoscopic surgery system 11000 through the inputting apparatus 11204. For example, the user would input an instruction or a like to change an image pickup condition (type of irradiation light, magnification, focal distance or the like) by the endoscope 11100.

A treatment tool controlling apparatus 11205 controls driving of the energy device 11112 for cautery or incision of a tissue, sealing of a blood vessel or the like. A pneumoperitoneum apparatus 11206 feeds gas into a body cavity of the patient 11132 through the pneumoperitoneum tube 11111 to inflate the body cavity in order to secure the field of view of the endoscope 11100 and secure the working space for the surgeon. A recorder 11207 is an apparatus capable of recording various kinds of information relating to surgery. A printer 11208 is an apparatus capable of printing various kinds of information relating to surgery in various forms such as a text, an image or a graph.

It is to be noted that the light source apparatus 11203 which supplies irradiation light when a surgical region is to be imaged to the endoscope 11100 may include a white light source which includes, for example, an LED, a laser light source or a combination of them. Where a white light source includes a combination of red, green, and blue (RGB) laser light sources, since the output intensity and the output timing can be controlled with a high degree of accuracy for each color (each wavelength), adjustment of the white balance of a picked up image can be performed by the light source apparatus 11203. Further, in this case, if laser beams from the respective RGB laser light sources are irradiated time-divisionally on an observation target and driving of the image pickup elements of the camera head 11102 are controlled in synchronism with the irradiation timings. Then images individually corresponding to the R, G and B colors can be also picked up time-divisionally. According to this method, a color image can be obtained even if color filters are not provided for the image pickup element.

Further, the light source apparatus 11203 may be controlled such that the intensity of light to be outputted is changed for each predetermined time. By controlling driving of the image pickup element of the camera head 11102 in synchronism with the timing of the change of the intensity of light to acquire images time-divisionally and synthesizing the images, an image of a high dynamic range free from underexposed blocked up shadows and overexposed highlights can be created.

Further, the light source apparatus 11203 may be configured to supply light of a predetermined wavelength band ready for special light observation. In special light observation, for example, by utilizing the wavelength dependency of absorption of light in a body tissue to irradiate light of a narrow band in comparison with irradiation light upon ordinary observation (namely, white light), narrow band observation (narrow band imaging) of imaging a predetermined tissue such as a blood vessel of a superficial portion of the mucous membrane or the like in a high contrast is performed. Alternatively, in special light observation, fluorescent observation for obtaining an image from fluorescent light generated by irradiation of excitation light may be performed. In fluorescent observation, it is possible to perform observation of fluorescent light from a body tissue by irradiating excitation light on the body tissue (autofluorescence observation) or to obtain a fluorescent light image by locally injecting a reagent such as indocyanine green (ICG) into a body tissue and irradiating excitation light corresponding to a fluorescent light wavelength of the reagent upon the body tissue. The light source apparatus 11203 can be configured to supply such narrow-band light and/or excitation light suitable for special light observation as described above.

FIG. 18 is a block diagram depicting an example of a functional configuration of the camera head 11102 and the CCU 11201 depicted in FIG. 17.

The camera head 11102 includes a lens unit 11401, an image pickup unit 11402, a driving unit 11403, a communication unit 11404 and a camera head controlling unit 11405. The CCU 11201 includes a communication unit 11411, an image processing unit 11412 and a control unit 11413. The camera head 11102 and the CCU 11201 are connected for communication to each other by a transmission cable 11400.

The lens unit 11401 is an optical system, provided at a connecting location to the lens barrel 11101. Observation light taken in from a distal end of the lens barrel 11101 is guided to the camera head 11102 and introduced into the lens unit 11401. The lens unit 11401 includes a combination of a plurality of lenses including a zoom lens and a focusing lens.

The number of image pickup elements which is included by the image pickup unit 11402 may be one (single-plate type) or a plural number (multi-plate type). Where the image pickup unit 11402 is configured as that of the multi-plate type, for example, image signals corresponding to respective R, G and B are generated by the image pickup elements, and the image signals may be synthesized to obtain a color image. The image pickup unit 11402 may also be configured so as to have a pair of image pickup elements for acquiring respective image signals for the right eye and the left eye ready for three dimensional (3D) display. If 3D display is performed, then the depth of a living body tissue in a surgical region can be comprehended more accurately by the surgeon 11131. It is to be noted that, where the image pickup unit 11402 is configured as that of stereoscopic type, a plurality of systems of lens units 11401 are provided corresponding to the individual image pickup elements.

Further, the image pickup unit 11402 may not necessarily be provided on the camera head 11102. For example, the image pickup unit 11402 may be provided immediately behind the objective lens in the inside of the lens barrel 11101.

The driving unit 11403 includes an actuator and moves the zoom lens and the focusing lens of the lens unit 11401 by a predetermined distance along an optical axis under the control of the camera head controlling unit 11405. Consequently, the magnification and the focal point of a picked up image by the image pickup unit 11402 can be adjusted suitably.

The communication unit 11404 includes a communication apparatus for transmitting and receiving various kinds of information to and from the CCU 11201. The communication unit 11404 transmits an image signal acquired from the image pickup unit 11402 as RAW data to the CCU 11201 through the transmission cable 11400.

In addition, the communication unit 11404 receives a control signal for controlling driving of the camera head 11102 from the CCU 11201 and supplies the control signal to the camera head controlling unit 11405. The control signal includes information relating to image pickup conditions such as, for example, information that a frame rate of a picked up image is designated, information that an exposure value upon image picking up is designated and/or information that a magnification and a focal point of a picked up image are designated.

It is to be noted that the image pickup conditions such as the frame rate, exposure value, magnification or focal point may be designated by the user or may be set automatically by the control unit 11413 of the CCU 11201 on the basis of an acquired image signal. In the latter case, an auto exposure (AE) function, an auto focus (AF) function and an auto white balance (AWB) function are incorporated in the endoscope 11100.

The camera head controlling unit 11405 controls driving of the camera head 11102 on the basis of a control signal from the CCU 11201 received through the communication unit 11404.

The communication unit 11411 includes a communication apparatus for transmitting and receiving various kinds of information to and from the camera head 11102. The communication unit 11411 receives an image signal transmitted thereto from the camera head 11102 through the transmission cable 11400.

Further, the communication unit 11411 transmits a control signal for controlling driving of the camera head 11102 to the camera head 11102. The image signal and the control signal can be transmitted by electrical communication, optical communication or the like.

The image processing unit 11412 performs various image processes for an image signal in the form of RAW data transmitted thereto from the camera head 11102.

The control unit 11413 performs various kinds of control relating to image picking up of a surgical region or the like by the endoscope 11100 and display of a picked up image obtained by image picking up of the surgical region or the like. For example, the control unit 11413 creates a control signal for controlling driving of the camera head 11102.

Further, the control unit 11413 controls, on the basis of an image signal for which image processes have been performed by the image processing unit 11412, the display apparatus 11202 to display a picked up image in which the surgical region or the like is imaged. Thereupon, the control unit 11413 may recognize various objects in the picked up image using various image recognition technologies. For example, the control unit 11413 can recognize a surgical tool such as forceps, a particular living body region, bleeding, mist when the energy device 11112 is used and so forth by detecting the shape, color and so forth of edges of objects included in a picked up image. The control unit 11413 may cause, when it controls the display apparatus 11202 to display a picked up image, various kinds of surgery supporting information to be displayed in an overlapping manner with an image of the surgical region using a result of the recognition. Where surgery supporting information is displayed in an overlapping manner and presented to the surgeon 11131, the burden on the surgeon 11131 can be reduced and the surgeon 11131 can proceed with the surgery with certainty.

The transmission cable 11400 which connects the camera head 11102 and the CCU 11201 to each other is an electric signal cable ready for communication of an electric signal, an optical fiber ready for optical communication or a composite cable ready for both of electrical and optical communications.

Here, while, in the example depicted, communication is performed by wired communication using the transmission cable 11400, the communication between the camera head 11102 and the CCU 11201 may be performed by wireless communication.

In the foregoing, the description has been given of one example of the endoscopic surgery system to which the technique according to the present disclosure may be applied. The technique according to the present disclosure may be applied to, for example, the endoscope 11100, the image pickup unit 11402 of the camera head 11102, etc. of the configurations described above. Specifically, any one of the imaging device 301 of FIG. 6 and the imaging device 601 of FIG. 10 to the imaging device 901 of FIG. 13 is applicable to the image pickup unit 11402. Applying the technique according to the present disclosure to the image pickup unit 11402 makes it possible to reduce a profile of the image pickup unit 11402 and thus to reduce the size thereof as well as to reduce the size of the camera head 11102 including the image pickup unit 11402.

It is to be noted that although the endoscopic surgery system has been described as an example here, the technique according to the present disclosure may also be applied to, for example, a microscopic surgery system, and the like.

The embodiments of the present technology are not limited to those described above, and may be modified in a wide variety of ways without departing from the gist of the present technology.

It is to be noted that the effects described in the present specification are merely illustrative and non-limiting, and there may be other effects other than those described in the present specification.

<Others>

The present technology may also have the following configurations.

(1)

An imaging device having a Wafer Level Chip Size Package structure including:

a semiconductor substrate in which a light receiving section is formed that includes a plurality of pixels performing photoelectric conversion; and a reinforcing member that is disposed on side of the light receiving section of the semiconductor substrate and includes an opening in which a part opposed to the light receiving section is opened.

(2)

The imaging device according to (1), in which the reinforcing member includes Si or glass.

(3)

The imaging device according to (1) or (2), in which the reinforcing member includes a light shield structure.

(4)

The imaging device according to (3), in which the reinforcing member includes the light shield structure on side, of the reinforcing member, opposite to side opposed to the light receiving section and in an end surface of the opening of the reinforcing member.

(5)

The imaging device according to (4), in which the reinforcing member further includes the light shield structure on side, of the reinforcing member, opposed to the light receiving section.

(6)

The imaging device according to any one of (1) to (5), in which the reinforcing member is disposed on the semiconductor substrate with a resin being interposed therebetween.

(7)

The imaging device according to (6), in which a thickness of the resin in the opening of the reinforcing member is thinner than a thickness of the resin in a part other than the opening.

(8)

The imaging device according to (6), in which the resin is provided only in a part other than the opening of the reinforcing member.

(9)

A camera module including:

an optical system that focuses light; and an imaging device having a Wafer Level Chip Size Package structure that receives the light to capture an image, the imaging device including
a semiconductor substrate in which a light receiving section is formed that includes a plurality of pixels performing photoelectric conversion, and
a reinforcing member that is disposed on side of the light receiving section of the semiconductor substrate and includes an opening in which a part opposed to the light receiving section is opened.

(10)
An electronic apparatus including:
an optical system that focuses light; and
an imaging device having a Wafer Level Chip Size Package structure that receives the light to capture an image, the imaging device including
a semiconductor substrate in which a light receiving section is formed that includes a plurality of pixels performing photoelectric conversion, and
a reinforcing member that is disposed on side of the light receiving section of the semiconductor substrate and includes an opening in which a part opposed to the light receiving section is opened.

REFERENCE NUMERALS LIST 1 imaging device
13 multilayer substrate
15 color filter
16 on-chip lens
17 glass seal resin
18 glass protective substrate
301 imaging device
310 semiconductor substrate
311 light receiving section
312 PAD
320 reinforcing member
320U upper surface
320E end surface
320D lower surface
321 opening
331 peripheral section
401 lens module
411 lens
412 lens barrel
413 actuator
501 lens module
511 lens
601 imaging device
602 light shield structure
701 imaging device
702 light shield structure
801, 901 imaging device

The invention claimed is:

1. An imaging device, comprising:
a semiconductor substrate including a light receiving section, wherein
the light receiving section includes a plurality of pixels configured to perform photoelectric conversion, and
the imaging device has a wafer level chip size package structure;
a reinforcing member on a side of the light receiving section of the semiconductor substrate, wherein the reinforcing member includes an opening in which a part of the reinforcing member opposed to the light receiving section is opened; and
a resin on the semiconductor substrate, wherein
a first portion of the resin is between the reinforcing member and the semiconductor substrate,
a second portion of the resin is on the light receiving section,
the second portion of the resin is in the opening, and
a thickness of the second portion of the resin in the opening is less than a thickness of the first portion of the resin.

2. The imaging device according to claim 1, wherein the reinforcing member further includes one of Si or glass.

3. The imaging device according to claim 1, wherein the reinforcing member further includes a light shield structure.

4. The imaging device according to claim 3, wherein
the light shield structure is on a first side of the reinforcing member opposite to a second side of the reinforcing member,
the second side of the reinforcing member is opposed to the light receiving section, and
the light shield structure is in an end surface of the opening of the reinforcing member.

5. The imaging device according to claim 4, wherein the light shield structure is on the second side of the reinforcing member opposed to the light receiving section.

6. A camera module, comprising:
an optical system configured to focus light; and
an imaging device configured to receive the light to capture an image, wherein
the imaging device has a wafer level chip size package structure,
the imaging device includes:
a semiconductor substrate including a light receiving section, wherein the light receiving section includes a plurality of pixels configured to perform photoelectric conversion,
a reinforcing member on a side of the light receiving section of the semiconductor substrate, wherein the reinforcing member includes an opening in which a part of the reinforcing member opposed to the light receiving section is opened, and
a resin on the semiconductor substrate,
a first portion of the resin is between the reinforcing member and the semiconductor substrate,
a second portion of the resin is on the light receiving section,
the second portion of the resin is in the opening, and
a thickness of the second portion of the resin in the opening is less than a thickness of the first portion of the resin.

7. An electronic apparatus, comprising:
an optical system configured to focus light; and
an imaging device configured to receive the light to capture an image, wherein
the imaging device has a wafer level chip size package structure,
the imaging device includes:
a semiconductor substrate including a light receiving section, wherein the light receiving section includes a plurality of pixels configured to perform photoelectric conversion,
a reinforcing member on a side of the light receiving section of the semiconductor substrate, wherein the reinforcing member includes an opening in which a part of the reinforcing member opposed to the light receiving section is opened, and
a resin on the semiconductor substrate,
a first portion of the resin is between the reinforcing member and the semiconductor substrate,
a second portion of the resin is on the light receiving section, the second portion of the resin is in the opening, and
a thickness of the second portion of the resin in the opening is less than a thickness of the first portion of the resin.

* * * * *